US008852211B2

(12) United States Patent
Mazzucco et al.

(10) Patent No.: US 8,852,211 B2
(45) Date of Patent: Oct. 7, 2014

(54) SURGICAL DEVICE

(75) Inventors: Dan Mazzucco, Haddon Heights, NJ (US); Eric Rugart, Wayne, PA (US); Jeffrey E. Ransden, Fairfield, CT (US); Alan B. Bachman, Milford, CT (US); Mark Nicosia, Chadds Ford, PA (US); Bob Cargill, West Deptford, NJ (US); Eric Butt, Orange, CT (US)

(73) Assignee: ZSX Medical, LLC, Philadelphia, PA (US)

( * ) Notice: Subject to any disclaimer, the term of this patent is extended or adjusted under 35 U.S.C. 154(b) by 402 days.

(21) Appl. No.: 13/115,246

(22) Filed: May 25, 2011

(65) Prior Publication Data
US 2011/0264118 A1    Oct. 27, 2011

Related U.S. Application Data

(63) Continuation-in-part of application No. PCT/US2010/031061, filed on Apr. 14, 2010.

(60) Provisional application No. 61/169,446, filed on Apr. 15, 2009, provisional application No. 61/300,127, filed on Feb. 10, 2010.

(51) Int. Cl.
| | |
|---|---|
| *A61B 17/10* | (2006.01) |
| *A61B 17/08* | (2006.01) |
| *A61B 17/00* | (2006.01) |
| *A61B 17/28* | (2006.01) |

(52) U.S. Cl.
CPC ...... *A61B 17/085* (2013.01); *A61B 2017/00004* (2013.01); *A61B 17/10* (2013.01); *A61B 17/2812* (2013.01); *A61L 2400/04* (2013.01); *A61L 2400/18* (2013.01); *A61B 2017/088* (2013.01); *A61B 17/083* (2013.01)
USPC .......................................... 606/142; 606/151

(58) Field of Classification Search
USPC ......... 606/157, 213, 215, 216, 219–221, 142, 606/151
See application file for complete search history.

(56) References Cited

U.S. PATENT DOCUMENTS

| | | | |
|---|---|---|---|
| 2,873,741 | A | 2/1959 | Donaldson |
| 2,932,296 | A | 4/1960 | Sanders |

(Continued)

FOREIGN PATENT DOCUMENTS

| | | |
|---|---|---|
| EP | 1270660 A1 | 1/2003 |
| WO | 2008101059 A2 | 8/2008 |

OTHER PUBLICATIONS

Whitehouse, et al., "The Impact of Surgical-Site Infections Following Orthopedic Surgery at a Community Hospital and a University Hospital: Adverse Quality of Life, Excess Length of Stay, and Extra Cost," Infection Control and Hospital Epidemiology, vol. 23, No. 4, pp. 183-189 (Apr. 2002).

(Continued)

*Primary Examiner* — Gregory Anderson
(74) *Attorney, Agent, or Firm* — Panitch Schwarze Belisario & Nadel LLP

(57) ABSTRACT

A wound closure device for closing a surgical wound is provided. The device includes a flexible base sheet and at least one flexible hemostatic clip for applying pressure to a patient's tissue. The flexible base sheet includes at least a first end and a second end, as well as an aperture extending through the base sheet longitudinally from proximate to the first end toward the second end. The aperture has a first and a second longitudinally extending edge. The clip has a first end, a second end, a top, a bottom, and at least a first and a second clamping member. Each clamping member has a distal edge. The clip is attachable to the base sheet.

14 Claims, 18 Drawing Sheets

(56) References Cited

U.S. PATENT DOCUMENTS

| | | | |
|---|---|---|---|
| 3,568,276 | A | 3/1971 | Morgan |
| 3,933,158 | A | 1/1976 | Haverstock |
| D252,496 | S | 7/1979 | Double |
| 4,217,902 | A | 8/1980 | March |
| 4,539,990 | A | 9/1985 | Stivala |
| 4,676,245 | A | 6/1987 | Fukuda |
| 4,706,661 | A | 11/1987 | Barrett |
| 4,796,627 | A | 1/1989 | Tucker |
| 4,905,694 | A | 3/1990 | Will |
| 5,002,562 | A * | 3/1991 | Oberlander .................. 606/221 |
| 5,026,389 | A | 6/1991 | Thieler |
| D331,462 | S | 12/1992 | Kraus et al. |
| 5,377,695 | A | 1/1995 | An Haack |
| 5,447,966 | A | 9/1995 | Hermes et al. |
| 5,779,720 | A | 7/1998 | Walder-Utz et al. |
| 5,916,224 | A | 6/1999 | Esplin |
| 6,106,544 | A | 8/2000 | Brazeau |
| 6,176,868 | B1 | 1/2001 | Detour |
| 7,112,214 | B2 | 9/2006 | Peterson et al. |
| D537,331 | S | 2/2007 | Hill |
| 2002/0111641 | A1 | 8/2002 | Peterson et al. |
| 2004/0073256 | A1 | 4/2004 | Marchitto et al. |
| 2004/0092968 | A1 | 5/2004 | Caro et al. |
| 2004/0133218 | A1 | 7/2004 | Charles et al. |
| 2004/0204724 | A1 | 10/2004 | Kissel et al. |
| 2004/0249414 | A1 | 12/2004 | Kissel et al. |
| 2005/0085757 | A1 | 4/2005 | Santanello |
| 2006/0052825 | A1 | 3/2006 | Ransick et al. |
| 2006/0241691 | A1 | 10/2006 | Wilk |
| 2007/0088339 | A1 | 4/2007 | Luchetti |
| 2008/0091277 | A1 | 4/2008 | Deusch et al. |
| 2008/0114396 | A1 | 5/2008 | Cory et al. |
| 2008/0228220 | A1 | 9/2008 | Weiser |
| 2009/0036922 | A1 | 2/2009 | Riskin et al. |
| 2009/0076542 | A1 | 3/2009 | Jonn et al. |
| 2010/0023056 | A1 * | 1/2010 | Johansson et al. ............ 606/232 |
| 2011/0034953 | A1 * | 2/2011 | Milo ............................. 606/213 |

OTHER PUBLICATIONS

Kirkland et al., "The Impact of Surgical-Site Infections in the 1990s: Attributable Mortality, Excess Length of Hospitalization, and Extra Costs," Infection Control and Hospital Epidemiology, vol. 20, No. 11, pp. 725-730 (Nov. 1999).

Perencevich et al., "Health and Economic Impact of Surgical Site Infections Diagnosed after Hospital Discharge," Emerging Infectious Diseases, vol. 9, No. 2, pp. 196-203 (Feb. 2003).

Mangram et al., "Guideline for Prevention of Surgical Site Infection," Infection Control and Hospital Epidemiology, vol. 20, No. 4, pp. 247-278 (Apr. 1999).

Cheadle W.G.,"Risk Factors for Surgical Site Infection," Surgical Infections, 7 Supp. 1:S7-11 (2006) (Abstrct only).

Edmiston et al, "Comparative of a New and Innovative 2% Chlorhexidine Gluconate-Impregnated Cloth with 4% Chlorhexidine Gluconate as Topical Antiseptic for Preparation of the Skin Prior to Surgery," American Journal of Infection Control, vol. 35, No. 2, pp. 89-96 (Mar. 2007) (Abstract only).

Rhee et al., "Reducing Surgical Site Infections," www.infectioncontroltoday.com (Mar. 1, 2008).

International Search Report dated Nov. 26, 2010 from the Korean Intellectual Property Office in International Application No. PCT/US2010/031061.

Witten Opinion dated Nov. 26, 2010 from the Korean Intellectual Property Office in International Application No. PCT/US2010/031061.

Extended European Search Report issued Dec. 2, 2013 in EP Application No. 10765104.4.

* cited by examiner

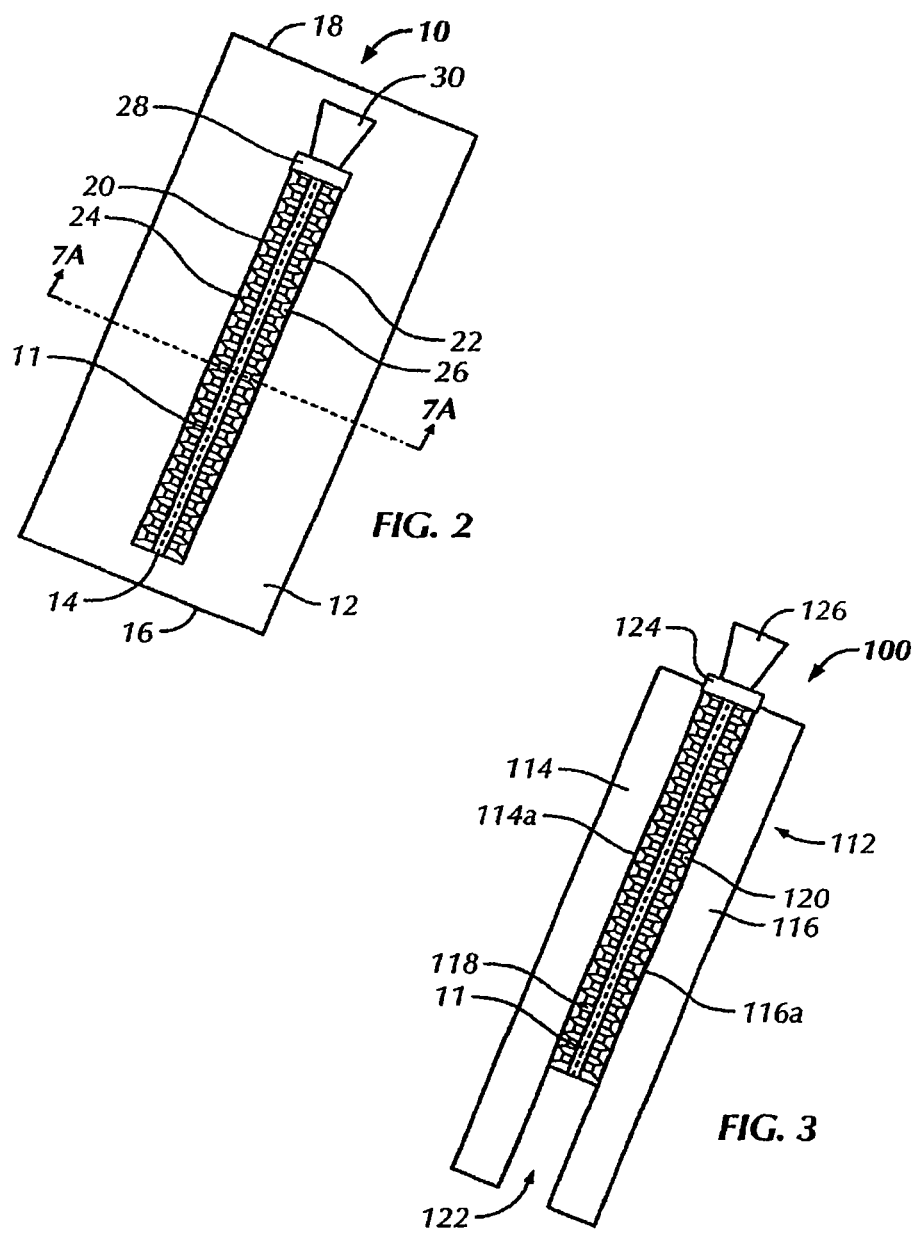

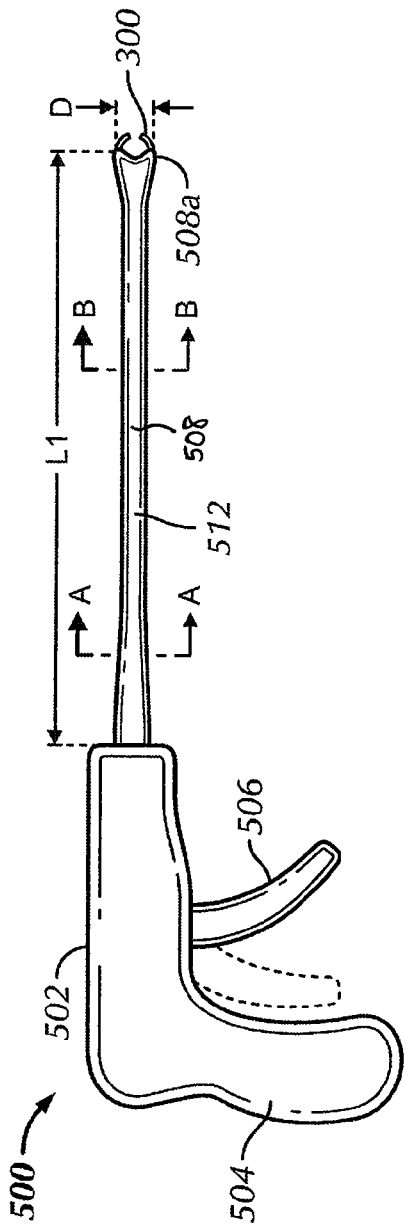
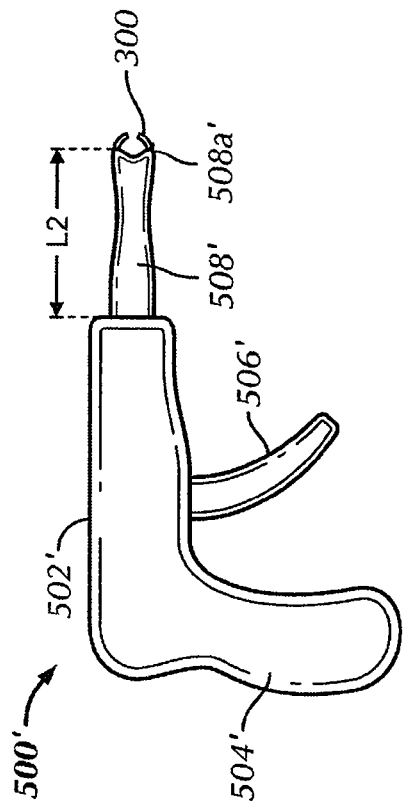
FIG. 24A
FIG. 24B

SURGICAL DEVICE

CROSS-REFERENCE TO RELATED APPLICATIONS

This application is a Continuation-In-Part of International Application No. PCT/US2010/031061, filed Apr. 14, 2010, which was published in the English language on Oct. 21, 2010, under International Publication No. WO 2010/120903 A2, and claims the benefit of U.S. Provisional Patent Application Nos. 61/169,446, filed on Apr. 15, 2009, entitled "Incision and Closure Device," and 61/300,127, filed on Feb. 1, 2010, entitled "Clip and Patch Closure Device," the disclosures of which are incorporated herein by reference.

BACKGROUND OF THE INVENTION

Existing methods and devices for creating and closing surgical incisions, particularly for surgical procedures involving soft tissue and internal organs, do not adequately protect patients from the associated health risks and complications, such as iatrogenic damage, ruptured organs, infections, tissue adhesion, and poor cosmetic appearance. Further, the current technology does not significantly decrease the time necessary to carry out many types of surgical procedures. Thus, the existing methods and devices do not reduce the various risks directly related to the duration of a surgical procedure.

Prior art methods and devices of closing surgical incisions include, for example, sutures, staples, tapes, and adhesives and energy-based sealants. However, these closure mechanisms are not sufficient prevention mechanisms against post-operative surgical site infections (SSI), the most common healthcare-associated infection in surgical patients. Patients who develop an SSI require significantly more medical care than those who are uninfected. For example, a surgical patient suffering from an SSI is 260 percent more likely to spend time in the intensive care unit after surgery than an uninfected patient. Further, a SSI increases the hospital length of stay for an infected patient by a median of two weeks. SSIs are particularly dangerous because they do not always develop immediately. Almost 2 percent of patients develop SSIs after they have been discharged from the hospital, and these patients are two to five times as likely to be readmitted to the hospital.

The prior art closure devices and methods suffer from several other deficiencies as well, particularly for certain types of procedures, such as those involving soft tissue and internal organs. Sutures may be risky because use can cause needlestick injury and subsequent infection to the medical personnel using them. Surgeons are also often faced with difficulty in repairing or closing incisions made for natural orifice trans-lumenal endoscopic surgery (NOTES), which results in lengthened surgery times and/or incision sites that have not been sufficiently hermetically sealed. Prior art devices also often fail to achieve proper post-operative healing, and may result in unsightly permanent scarring. Further, for procedures requiring subsequent and repeated access to the incision site, such access is often difficult when the incision has been closed with prior art mechanisms. Finally, the prior art closure mechanisms often involve multi-stage procedures and, thus, an additional hospital visit is typically required for removal of the closure mechanism.

Prior art devices and methods for making incisions also suffer from various additional deficiencies. With respect to caesarian procedures in particular, there have been reports of babies delivered by caesarian section who have been cut or wounded by the surgical incision device during the procedure. Further, it is often difficult for surgeons to make incisions for NOTES to gain laparotic entry through the internal organs of concern, without risking damage to other internal organs. Thus, there is an increase in the overall surgery time and an associated increase in the surgical risks and complications. Another type of surgical procedure for which prior art devices and methods are inadequate is a tubal resectioning procedure. Such procedures can take up to 10 hours because it can be difficult to make the accurate type of initial incision on dual lumen tubes as is necessary for perfect tissue presentation for closure.

Thus, there is a need for an incision device and a closure device, particularly for internal organ and soft tissue procedures, which enables medical personnel to efficiently and accurately create and close an incision, respectively, thus decreasing the overall length of time for a surgical procedure and the risk of infection. There is a further need for a closure device that achieves the necessary hermetic seal for organs and tissue which have been cut, thus resulting in a reduced risk of post-operative infections. There is also a need for a permanent closure mechanism that does not have to be subsequently removed by medical personnel, thus eliminating the need for an additional hospital visit and removal procedure.

BRIEF SUMMARY OF THE INVENTION

The present invention, in one embodiment, is directed to a wound closure device for closing a surgical wound. The device includes a flexible base sheet and at least one flexible hemostatic clip for applying pressure to a patient's tissue. The flexible base sheet includes at least a first end and a second end, as well as an aperture extending through the base sheet longitudinally from proximate to the first end toward the second end. The aperture has a first and a second longitudinally extending edge. The clip has a first end, a second end, a top, a bottom, and at least a first and a second clamping member. Each clamping member has a distal edge. The clip is attachable to the base sheet.

In a further aspect, the present invention relates to a clipping mechanism comprising a plurality of flexible hemostatic clips. Each clip has a first end, a second end, a top and a bottom. The bottom of each clip includes an indentation formed at the first end of the clip and a finger extending generally outwardly from the second end of the clip.

In another aspect, the present invention is directed to a wound incision and closure device including at least one flexible base sheet having a first and a second end; an aperture extending through the base sheet longitudinally from proximate to the first end of the base sheet toward the second end of the base sheet; a plurality of fastening elements disposed at spaced-apart locations along substantially an entire length of each of the first and second longitudinally extending edges of the aperture; and a slider longitudinally displaceable along the plurality of fastening elements. The aperture has a first and a second longitudinally extending edge and the plurality of fastening elements are reversibly engageable with each other. The plurality of fastening elements engage each other when the slider is moved in a first longitudinal direction for closing the surgical wound and the plurality of fastening elements disengage from each other when the slider is moved in a second longitudinal direction for exposing the surgical wound.

In a further aspect, the present invention relates to a method of closing a surgical wound including the steps of: attaching to a patient's tissue a flexible base sheet including a first end, a second end and an aperture extending through the base sheet longitudinally from proximate to the first end toward the second end and having a first and a second longitudinally extending edge; incising at least a portion of the tissue between the first and second longitudinally extending edges; and attaching to the base sheet at least one flexible hemostatic clip. The clip has a first end, a second end, a top, a bottom, and at least a first and a second clamping member each with a distal end. The first clamping member of the clip is oriented on the base sheet proximate to the first longitudinally extending edge and the second clamping member of the clip is oriented on the base sheet proximate to the second longitudinally extending edge, such that a first projection extending from the distal edge of the first clamping member engages a pocket formed on the base sheet proximate to the first longitudinally extending edge and a second projection extending from the distal edge of the second clamping member engages a pocket formed on the base sheet proximate to the second longitudinally extending edge. The first and second clamping members of the clip bring edges of the incised tissue toward each other.

In a further aspect, the present invention relates to a method of making an incision and closing the resulting incision. The method includes the steps of: attaching to a patient's tissue a flexible base sheet including an aperture extending through the base sheet longitudinally from proximate to a first end of the base sheet toward a second end of the base sheet; incising at least a portion of the tissue between the first and second longitudinally extending edges of the aperture; and longitudinally displacing a slider along the plurality of fastening elements in a first longitudinal direction to bring the first longitudinally extending edge toward the second longitudinally extending edge for closing of the incision. The aperture has a first and a second longitudinally extending edge and a plurality of fastening elements are disposed at spaced apart locations along substantially an entire length of each of the first and second longitudinally extending edges of the aperture. Each of the first and second longitudinally extending edges are aligned with an incision to be made. The plurality of fastening elements engage each other when the slider is moved in the first longitudinal direction.

In another aspect, the present invention relates to a wound closure device for closing a surgical wound. The device comprises at least one flexible and bio-absorbable hemostatic clip for applying pressure to a patient's tissue. The clip comprises at least a first clamping member having a first distal edge and a second clamping member having a second distal edge. The first and second distal edges are provided with a plurality of spaced-apart clamping teeth. The clip is directly attachable to the patient's tissue.

BRIEF DESCRIPTION OF THE SEVERAL VIEWS OF THE DRAWINGS

The following detailed description of the preferred embodiments of the present invention will be better understood when read in conjunction with the appended drawings. For the purposes of illustrating the invention, there are shown in the drawings embodiments which are presently preferred. It is understood, however, that the invention is not limited to the precise arrangements and instrumentalities shown. In the drawings:

FIG. 2 is a top plan view of the surgical device shown in FIG. 1A in an open position;

FIG. 3 is a top plan view of a surgical device in accordance with a second preferred embodiment of the present invention;

FIG. 24A is a side elevational view of a second type of applicator for the clipping mechanism shown in FIGS. 20-21;

FIG. 24B is a side elevational view of a third type of applicator for the clipping mechanism shown in FIGS. 20-21;

DETAILED DESCRIPTION OF THE INVENTION

Figure 1A:
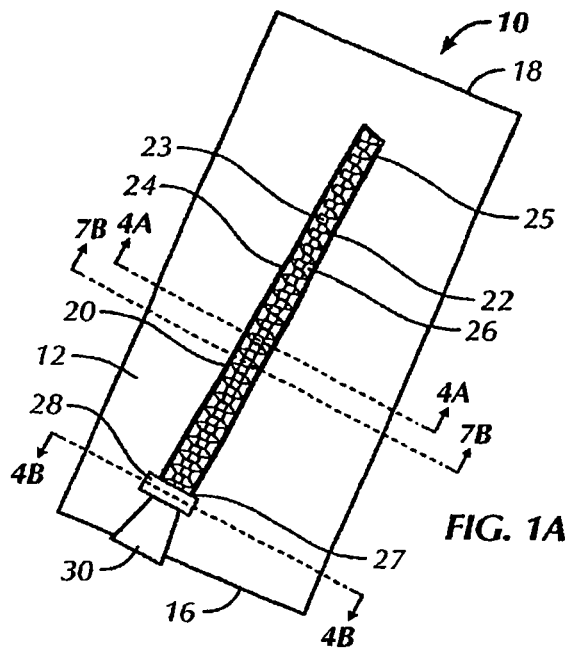
FIG. 1A is a top plan view of a first preferred embodiment of the surgical device of the present invention in a closed position.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the device and designated parts thereof. Unless specifically set forth herein, the terms "a", "an" and "the" are not limited to one element but instead should be read as meaning "at least one". The terminology includes the words noted above, derivatives thereof and words of similar import.

Figure 1B:
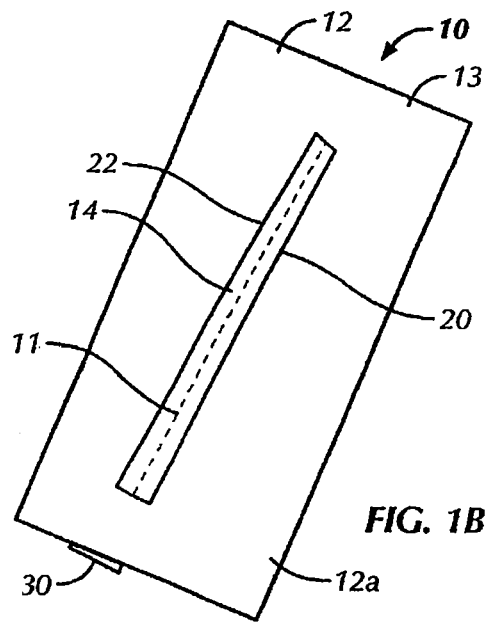
FIG. 1B is a bottom plan view of the surgical device shown in FIG. 1A.

Referring to the drawings in detail, wherein like numerals and characters indicate like elements throughout, there is shown in FIGS. 1A-2 an incision and closure device 10 in accordance with a first preferred embodiment of the present invention. With reference to FIGS. 1A-2, the incision and closure device 10, includes a base or base sheet 12 and a slider mechanism 28.

The incision and closure device 10 is a surgical device and includes a linear aperture 14 formed in the base 12. The aperture extends through the base 12 longitudinally from proximate to a first end 16 toward a second end 18 of the base 12. The aperture 14 is further defined by a first longitudinally extending edge 20 and a second longitudinally extending edge 22. The device 10 may be used to make or close incisions in bone, cutaneous tissue, subcutaneous tissue, including soft tissue, and internal organs.

The base 12 preferably has a single body construction, as shown in FIGS. 1A-2, such that the aperture 14 is formed in the body of the base 12. Preferably, the base 12 is flexible so that the device 10 may conform to the contours of a patient's bone, cutaneous tissue, subcutaneous tissue, and internal organs. Accordingly, in an attached or use position, the shape of the base 12 conforms with the contours of the patient's tissue. If the contours of the patient's tissue are planar, then the base 12 will have a planar shape in the use or attached position. If the contours of the patient's tissue are curved, such as with an internal organ, then the base 12 will appear to have a curved shape in the use or attached position. It will be understood by those skilled in the art that while the base 12 shown in FIGS. 1A-2 has a generally rectangular shape and the aperture 14 is generally linear, the base 12 and aperture 14 may be of any shape or size necessary to meet the situational demands of the particular surgical procedure to be performed.

The base 12 is preferably bio-absorbable and may be made of a material that is absorbable by human or animal tissue, and resistant to the formation of tissue adhesions. For example, the base may be made of hyaluronic acid, carboxymethylcellulose, hydrolytically-degradable polyester urethane, oxidized regenerated cellulose, poly glycolic acid (PGA), poly lactic acid (PLA), poly lactic co-glycolic acid (PLGA), poly malic acid, poly (isobutyl cyanoacrylate), poly-p-dioxanone (PDS), poly (glycolide-trimethylene carbonate) (GTMC), poly-(glycolide-caprolactone) (PCL), nucleic acids, collagen, chitosan, fibrin, or other polypeptides.

A chain 23 comprising a plurality of fastening elements 24, 26 extends through the base 12. Preferably, the plurality of fastening elements 24, 26 are bio-absorbable. Specifically, the chain 23 includes a first set of bio-absorbable fastening or interlocking members 24 and a second set of corresponding bio-absorbable fastening interlocking members 26 disposed at spaced-apart locations along substantially an entire length of each of the first and second longitudinally extending edges 20, 22 of the aperture 14, respectively. The first set of interlocking members 24 disposed along the first longitudinally extending edge 20 are reversibly engageable with the second set of interlocking members 26 disposed along the second longitudinally extending edge 22 to form the chain 23. As shown in FIG. 1A, the chain 23 of interlocking members 24, 26 covers the aperture 14 when the device 10 is in a closed position—i.e., when the first and second set of interlocking members 24, 26 are engaged with each other. When the first and second set of interlocking members 24, 26 are disengaged from each other, the device 10 is in the open position and the aperture 14 is exposed, as shown in FIG. 2.

Any appropriate interlocking structure may be used as the first and second set of interlocking members 24, 26. For example, the first and second set of interlocking members 24, 26 may be formed as conventional interlocking teeth, corresponding male and female components, or interlocking channels, such as those found on a plastic zip-type bag. In FIGS. 1A-2, the first and second set of interlocking members 24, 26 are shown as interlocking teeth, such as those found on a conventional zipper mechanism. The first and second set of interlocking members 24, 26 may be brought into contact with each other by any conventional means.

Preferably, a slider mechanism 28 is provided which is longitudinally displaceable along the first and second set of interlocking members 24, 26 to bring the first and second set of interlocking members 24, 26 into alignment and engagement with or disengagement from each other. When the slider mechanism 28 is moved in a first longitudinal direction, traversing the length of the chain 23 from a first end 25 to a second end 27 of the chain 23, the first and second set of interlocking members 24, 26 engage each other for closing of a surgical wound or incision 33. When the slider mechanism 28 is moved in a second longitudinal direction, traversing the length of the chain 23 from the second end 27 to the first end 25 of the chain 23, the first and second set of interlocking members 24, 26 disengage from each other for exposing the aperture 14 and the surgical wound or incision 33. It will be understood by those skilled in the art that the terms first end and second end are merely being used here for illustrative purposes and that the opposite meaning may be associated with each end. The slider mechanism 28 is preferably equipped with a pull tab 30 to facilitate the sliding operation of the slider mechanism 28. Alternatively, the first and second set of interlocking members 24, 26 may be manually manipulated by the operator or some external device to be brought into alignment and contact with one another.

Referring to FIG. 3, there is shown an incision and closure device 100 in accordance with a second preferred embodiment of the present invention. The incision and closure device 100 comprises a flexible base or base sheet 112 formed from a first elongated base member 114 and a second elongated base member 116. The first base member 114 has a first longitudinally extending edge 114a equipped with a first set of interlocking members 118. The second base member 116 has a second longitudinally extending edge 116a equipped with a second set of corresponding interlocking members 120. The first set of interlocking members 118 are capable of actively engaging and disengaging from the second set of interlocking members 120. When the first and second base members 114 and 116 are properly situated at aligned spaced locations on a patient's bone or tissue, an aperture or channel 122 is formed between the first and second elongated base members 112 and 114, respectively. A slider mechanism 124 and a pull tab 126 are further provided and connected to the first longitudinally extending edge 114a, though these components may alternatively be provided on second edge 116a. The first and second longitudinally extending edges 114a and 116a, respectively, may be brought into alignment and contact with one another in the same manner as described above for the embodiment of FIGS. 1A-2.

Figure 4A:
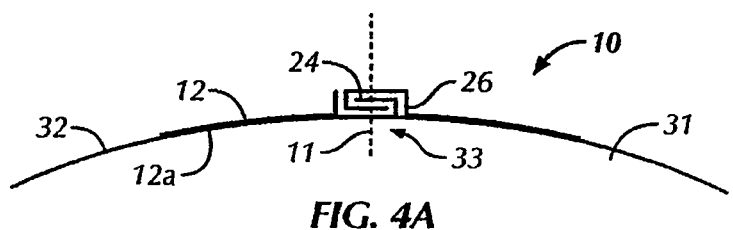
FIG. 4A is a cross-sectional view of the surgical device shown in FIG. 1A taken along line 4A-4A of FIG. 1A attached to the uterus of a human surgical patient.

During a surgical procedure, the device 10, 100 is attached to a patient's tissue 31 in an area of the tissue 31 to be incised and/or closed. Referring to FIG. 4A, the device 10 is shown attached to an internal organ, such as the uterus 32 of a human surgical patient, which is to be incised and the incision to be subsequently closed. While the uterus 32 of a human patient is used for illustrative purposes in the present embodiment, it would be apparent to one of ordinary skill in the art that the device 10, 100 may be employed on any type of mammalian tissue, including any type of organ such as a kidney, lung, liver, heart, etc.

A first side 12a of the base 12 is provided for contact with the patient's tissue 31. The base 12 is to be oriented along the intended line of incision 11. When properly situated, the first and second longitudinally extending edges 20, 22 of the aperture 14 align with the incision 33 to be made. Next, at least a portion of the tissue 31 aligned with the first and second longitudinally extending edges 20, 22 may be incised. This can be accomplished in a variety of ways.

Figure 4B:
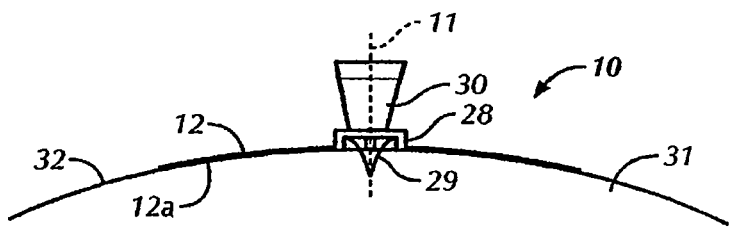
FIG. 4B is a cross-sectional view of the surgical device shown in FIG. 1A taken along line 4B-4B of FIG. 1A attached to the uterus of a human surgical patient while the slider mechanism is traversing the length of the chain 23.
Figure 5:
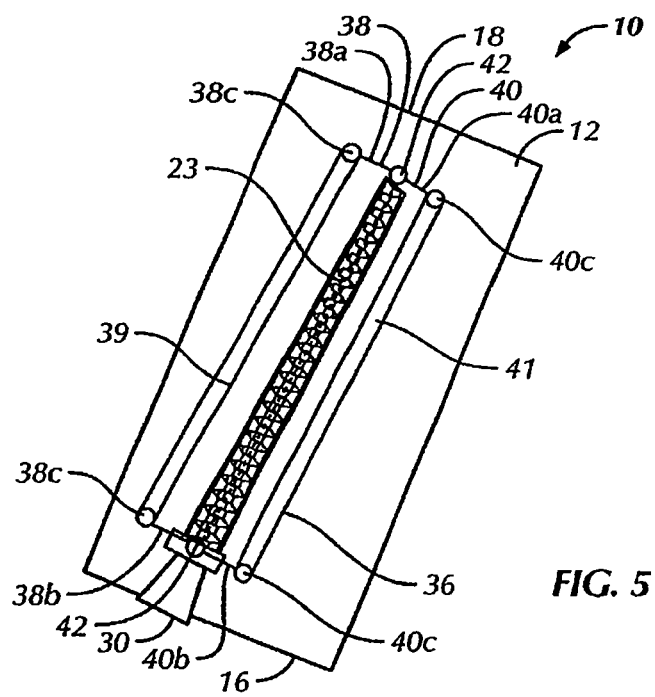
FIG. 5 is a top plan view of the surgical device shown in FIG. 1A further comprising a clamping mechanism.

Referring to FIG. 4B, the slider mechanism 28 may equipped with an incising instrument or cutting mechanism 29. Specifically, a surgical blade or other appropriate instrument may be embedded within the slider mechanism 28 or, alternatively, the edge of the slider mechanism 28 that is in contact with the patient's tissue 31 may be formed as a cutting edge. The cutting mechanism 29 aligns with the aperture 14. Thus, when the device 10 is attached to the tissue 31 to be incised and the incision subsequently to be closed, the device 10 is oriented on the tissue along the intended line of incision 11 in the closed position, such that the chain 23 of the first and second set of interlocking members 24, 26 and the first and second longitudinally extending edges 20, 22 of the aperture 14 are aligned with the intended line of incision 11 (sees FIG. 4A). As such, the chain 23 of the first and second set of interlocking members 24, 26 serves as a guide for making the desired incision 33. Once the device 10 is oriented properly and secured to the tissue 31, the incision 33 may be made by simply longitudinally displacing or traversing the slider mechanism 28 in the second longitudinal direction from the second end 27 to the first end 25 along the chain 23 of interlocking members 24, 26. Thus, while the slider mechanism 28 is in its traversal pattern, the cutting mechanism 29 extends into the patient's tissue 31 to make the desired incision 33, as shown in FIG. 4B, and the first and second set of interlocking members 24, 26 disengage from each other to expose the resulting incision 33.

Alternatively, the device 10, 100 may be oriented along the intended line of incision 11 in the open position, such that the first and second set of interlocking members 24, 26 are disengaged from each other and the aperture 14 is aligned with the intended line of incision 11 (see FIGS. 2-3). As such, the aperture 14 or channel 122 serves as a guide for making the desired incision 33. A conventional surgical instrument, such as a scalpel, may be used to make the incision 33 by simply following the length of the aperture 14 or channel 122.

The slider mechanism 28 may alternatively be provided with an alignment or positioning mechanism (not shown) to position the surgical instrument laterally. A surgical instrument, such as a scalpel, may be inserted through the alignment or positioning mechanism and guided by the slider mechanism 28 and the alignment or positioning mechanism to make the desired incision 33 within the aperture 14. The alignment or positioning mechanism may also be adapted to control the depth to which the incision 33 is made, and may be provided with stops or other adjustment mechanisms by which successive incisions at increasing or decreasing depths may be made in successive traversals, depending on the situational demands of the particular surgical procedure to be performed.

Closure of the device 10, 100 may be simply achieved by longitudinally displacing the slider mechanism 28 in the first longitudinal direction from the first end 25 to the second end 27 along the chain 23 of the first and second set of interlocking members 24, 26, such that the first and second set of interlocking members 24, 26 engage each other to bring the first and second longitudinally extending edges 20, 22 of the aperture 14 toward each other for closing of the incision 33. When the slider mechanism 28 is moved in a second longitudinal direction, traversing the length of the chain 23 from the second end 27 to the first end 25 of the chain 23, the first and second set of interlocking members 24, 26 disengage from each other for exposing the aperture 14 and the surgical wound or incision 33.

The device 10, 100 may further comprise a clamping mechanism 36, as shown in FIGS. 5 and 6A-6C, for applying pressure to the patient's tissue 31. Preferably, the clamping mechanism 36 is reversibly attachable to the base 12, 112 and comprises a first clamping member 38 which is pivotally connected to a second clamping member 40. Specifically, the first clamping member 38 includes a first clamping arm 38a and a second clamping arm 38b. The second clamping member 40 includes a third clamping arm 40a and a fourth clamping arm 40b. The first and second clamping members 38 and 40, respectively, are connected to each other at a pivot point or fulcrum 42 at the first and second ends of 16, 18 of the base 12. A first tubular member 39 is secured proximate to the distal ends 38c of the first and second clamping arms 38a, 38b, and extends therebetween, such that the first and second clamping arms 38a, 38b are connected with each other. A second tubular member 41 is secured proximate to the distal ends 40c of the third and fourth clamping arms 40a, 40b, and extends therebetween, such that the third and fourth clamping arms 40a, 40b are connected with each other. Specifically, the first and second tubular members 39 and 41, respectively, extend in a direction parallel to the chain 23 of the first and second set of interlocking members 24, 26.

Figure 6A:
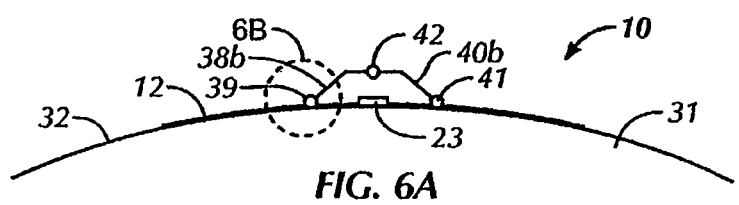
FIG. 6A is a front view of the surgical device shown in FIG. 5 as the clamping mechanism is placed on the uterus of a human surgical patient.

The first and second tubular members 39 and 41 are preferably compression-fit hollow hemicylinders and extend along the entire length of the intended line of incision 11. The first and second clamping members 38 and 40 are preferably comprised of spring wire or other biasing component, and have a relaxed or closed position as shown in FIG. 6C. While the present invention is only described as comprising four clamping arms 38a, 38b, 40a and 40b, as well as two tubular members 39 and 41, it will be understood by those skilled in the art that the clamping mechanism 36 may comprise more than four clamping arms and more than two tubular members. For example, in an alternate embodiment (not shown), the tubular members 39, 41 do not continuously extend along the entire length of the intended line of incision 11. Instead, the clamping mechanism 36 comprises a plurality of spaced apart tubular members that extend along portions of the length of the intended line of incision 11 by a plurality of spaced-apart, pivotally connected clamping arms.

Figure 6B:
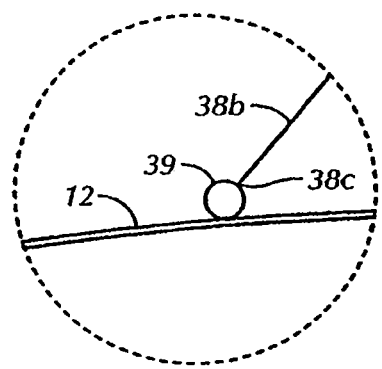
FIG. 6B is a greatly enlarged view of the clamping mechanism shown in FIG. 6A taken about area 6B.
Figure 6C:
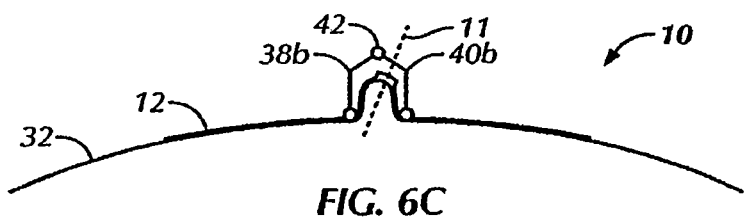
FIG. 6C is a front view of the surgical device shown in FIG. 5 after the clamping mechanism has been placed on the uterus of a human surgical patient.

The clamping mechanism 36 is reversibly attached to the base 12 by the first and second tubular members 39 and 41, as shown in FIG. 6B, prior to making of the incision 33. When the device 10 comprising the clamping mechanism 36 is properly placed on the patient's tissue 31 and the base 12, the first and second tubular member 39 and 41, respectively, are oriented on either side of the intended line of incision 11, such that the first and second tubular members 39 and 41 extend in a direction parallel to the intended line of incision 11 and the chain 23 of interlocking members 24, 26. The first and second tubular members 39 and 41 may be oriented equidistantly from the intended line of incision 11 or may be offset from the center of the intended line of incision 11.

Before placement of the clamping mechanism 36 on the patient's tissue 31, the first and second clamping members 38, 40 are manually spread apart from each other, as shown in FIG. 6A. Specifically, the first clamping arm 38a is spread apart from the opposing and third clamping arm 40a, and the second clamping arm 38b is spread apart from the opposing and fourth clamping arm 40b. When the clamping mechanism 36 is placed on the patient's tissue 33, the first and second clamping members 38, 40 are biased to automatically come together. This action causes the first and second tubular members 39 and 41 to apply pressure to the patient's tissue 31 around the intended line of incision 11. The resulting pressure serves to fold and clamp the patient's tissue 31 prior to incision, as shown in FIG. 6C. This clamping action also applies positive pressure to the tissue 31, which reduces the blood content of the tissue and minimizes blood loss upon cutting of the tissue 31.

When the tissue 31 has been properly clamped, the fulcrum 42 of the clamping mechanism 36 is disposed above the clamped tissue 31 and is spaced far enough from the clamped tissue 31 to allow incising of the clamped tissue 31. The slider mechanism 28 may then be used to make an incision 33 through the clamped tissue 31. Alternatively, a conventional instrument may be used to incise the clamped tissue 31 at an angle from either side of the clamped tissue 31. The clamping mechanism 36 maintains positive pressure on the tissue 31 until the internal procedure is complete or until hemostasis is achieved. For example, if the device 10 is being used for a tubal resectioning procedure, the clamping mechanism 36 maintains positive pressure on the tissue 31 until anastomosis.

Use of the device 10, 100 thus allows for a controlled and precise incision to be made upon bone, soft tissue and internal organs without risk of accidental or unintended damage to the surrounding tissue and organs. Specifically, because the slider mechanism 28 of the device 10 may have a cutting mechanism 29 embedded therein or because the aperture 14 may serve as a guide for incision, the danger of a surgeon accidentally cutting into any of the tissue 31 surrounding the intended line of incision 11 or cutting deeper into the tissue 31 than is intended is greatly reduced or even eliminated. Because the device 10 allows for such accurate and precise incisions, it is ideally suited for numerous internal organ procedures, such as natural orifice trans-lumenal endoscopic surgeries, caesarian sections, and tubal ligation or resectioning procedures.

For a tubal resectioning procedure, in particular, a device 10, 100 may be adhered to the tissue of the lumen tube to be resectioned at each intended point of severance. Thus, one or more devices 10, 100 may be used for initial severance of the lumen tubes and a further device 10, 100 may be used to join the resected tissue. Since the slider mechanism 28 may have an embedded cutting mechanism 29 (see FIG. 4B), a precise and accurate line of incision or severance may be made at the end of each section of the lumen tube, so as to ensure perfect tissue presentation for joining of the resected tissue. Thus, the lumen tubes may easily be severed and the severed tissue may easily be resectioned and joined by the device 10 without the risk of damage to the surrounding tissue and organs.

Figure 7A:
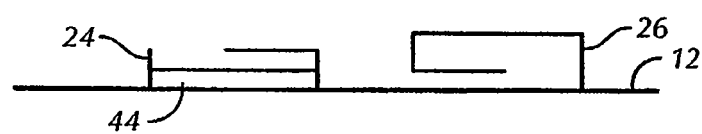
FIG. 7A is a cross-sectional schematic view of the surgical device shown in FIG. 2 taken along line 7A-7A of FIG. 2, further comprising a channel for beneficial agents.
Figure 7B:
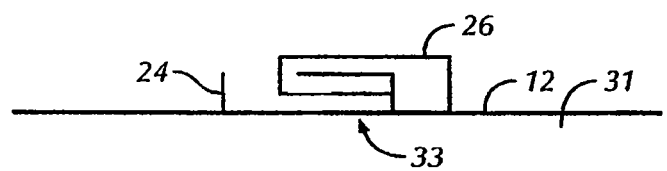
FIG. 7B is a cross-sectional schematic view of the surgical device shown in FIG. 1A taken along line 7B-7B of FIG. 1A, further comprising a channel for beneficial agents.

After the necessary surgical procedures have been performed, the device 10, 100 may further be utilized to close the incision 33 by simply traversing the slider mechanism 28 from the first end 25 to the second end 27 of the chain 23, thereby pulling the edges of the incised tissue 31 toward each other. During closure of the wound or incision 33, preferably one or more therapeutic pharmaceutical, antimicrobial or restorative agents may be applied into and/or onto the wound or incision 33. When the device 10, 100 is in the open position, such agents may be disposed within a bottom channel 44 of the either the first or second set of interlocking members 24 or 26 (shown in FIG. 7A). However, when the device 10, 100 is placed into the closed position, during closure of the wound or incision 33, moving the sliding mechanism 28 in the first longitudinal direction causes the opposed first and second set of interlocking members 26 or 24 to displace the therapeutic agents in the channel 44, such that the agents are be deposited into and/or onto the wound or incision 33 (shown in FIG. 7B).

Any type of agent that may be beneficial in the surgical or post-surgical environment may be applied to the wound by such a configuration. Examples of such agents include adhesives, antibiotics, soaps, degradation-inducing components, anesthetics, healing-promoters (e.g., growth factors or collagens), protectants (e.g., antioxidants), clotting promoters, clotting inhibitors, hyaluronic acid, natural or synthetic plant extracts or distillates, natural or synthetic animal extracts or distillates, natural or synthetic mineral extracts or distillates (e.g., honey, lobelia extracts, saliva proteins, isolated proteins, silver, titanium dioxide or copper antibacterial preparations), bone cements, stem cell preparations, vascular pastes, analgesics, wet or drying agents (e.g., desiccants, absorbables, foams), heating or cooling agents, staining agents, cosmetic agents, diagnostic agents, shielding agents, and hair growth or retardation agents. Further, such agents may include natural or synthetic bodily tissues, as prepared or combined ingredients, which are actively sprayed, spread or deposited into and/or onto the wound upon closure, or which are passively emitted via decomposition, degradation or activation following the application of the device 10, 100.

Figure 8:
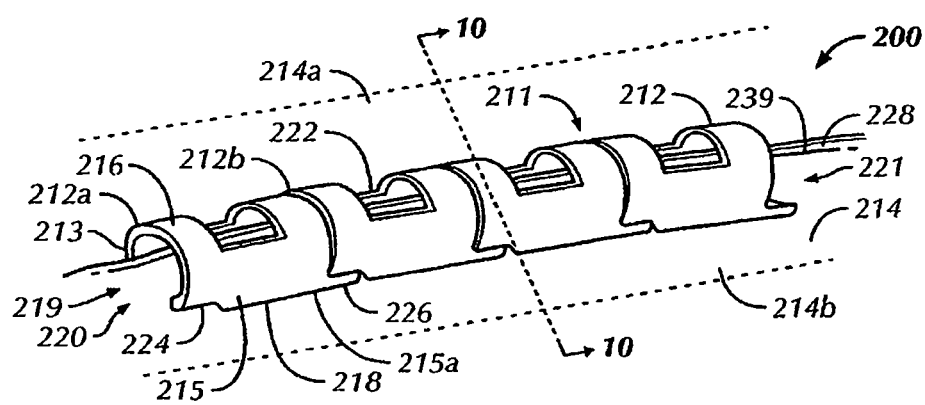
FIG. 8 is a top right perspective view of a third preferred embodiment of the surgical device of the present invention in an assembled and closed position.
Figure 9:
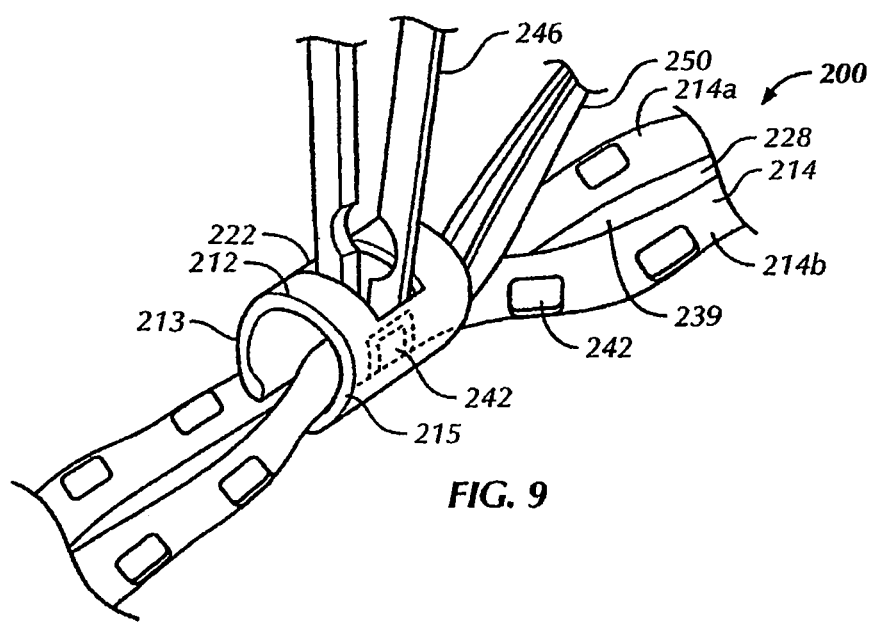
FIG. 9 is a top right perspective view of the surgical device shown in FIG. 8 as a clipping mechanism of the present invention is being placed on the tissue of a human surgical patient.
Figure 10:
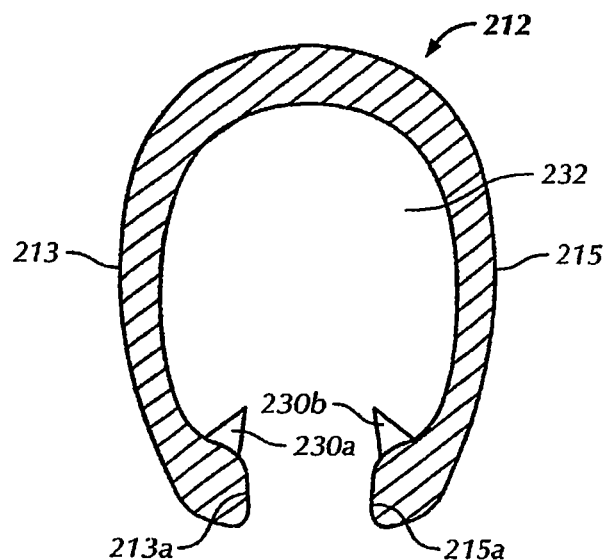
FIG. 10 is a cross-sectional view of a clipping mechanism of the surgical device shown in FIG. 8 taken along line 10-10 of FIG. 8.
Figure 11:
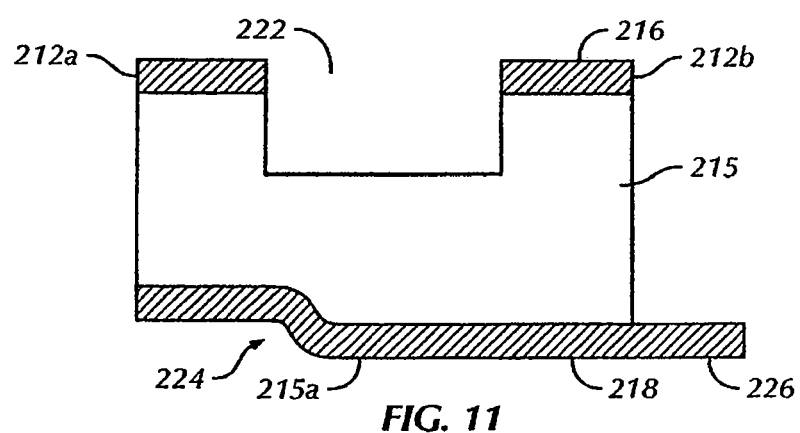
FIG. 11 is an axial cross-sectional view of a clipping mechanism of the surgical device shown in FIG. 8.

Referring to FIGS. 8-9, a wound closure mechanism 200 in accordance with a third preferred embodiment of the present invention is shown. The closure mechanism 200 comprises a clipping mechanism 211 and a base sheet or base sheet 214. Preferably, both the clipping mechanism 211 and the base sheet 214 of the closure device 200 are made from a flexible and elastic adhesion-resistant bio-absorbable material. Referring to FIGS. 8 and 10-11, the clipping mechanism 211 comprises a plurality of hemostatic clips 212 for applying pressure to a patient's tissue 220. Each clip 212 has an elongated shape and comprises a one-piece clip comprising a first end 212a, a second end 212b, a top 216 and a bottom 218. Specifically, each clip 212 has a generally C-shaped cross-section (see FIG. 10). While the term "clip" is used herein to describe a component of the clipping mechanism 211, it will be understood by those skilled in the art that the clip 212 essentially functions as a clamp, and thus may be referred to as a clamp or any other appropriate name.

Each clip 212 is attachable to the base sheet 214. Preferably, each clip 212 is reversibly attachable to the base sheet 214. Specifically, the bottom 218 of each clip 212 clamps a surgical patient's tissue 220 when the closure device 200 is placed on the base sheet 214 and the patient's tissue 220. An elongated aperture or opening 222 is formed in the top 216 of each clip 212. The opening 222 enables a surgeon or other medical professional applying the clip 212 to a patient's tissue 220 to clearly view the tissue 220. The opening 222 extends laterally from a location proximate the first end 212a toward the second end 212b of the clip 212. At the bottom 218 of the clip 212, a recess or an indentation 224 is formed at the first end 212a and a finger 226 extends generally outwardly away from the second end 212b of the clip (see FIG. 11). Referring to FIG. 11, the indentation 224 extends from a distal edge of the first end 212a of the clip 212 toward the second end 212b of the clip 212. The finger 226 is of a generally linear shape and of a similar size as the indentation 224. Specifically, the indentation 224 of a first clip 212 is configured to receive the finger 226 of a second clip 212, as described in more detail below.

Accordingly, the design of the clip 212 enables multiple clips 212 to be positioned in an overlapping or engaging configuration, as the finger 226 of a first clip 212 engages or nests within the indentation 224 of a second clip 212 positioned immediately thereafter, in an assembled configuration of the clipping mechanism 211 (see FIG. 8). More particularly, a plurality of clips 212 may be arranged in such an overlapping or engaging manner along a length of a wound or incision 228, such that there are little or no areas of unclamped tissue, thereby ensuring complete closure of the wound or incision 228.

Figure 12A:
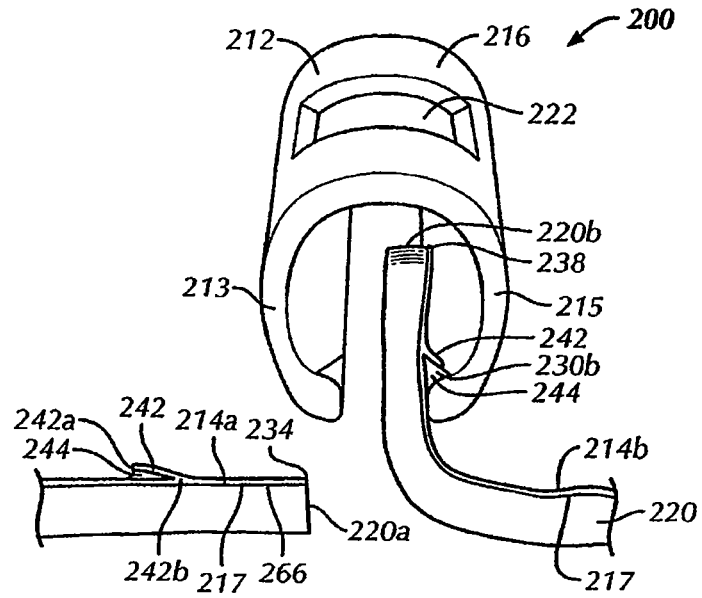
FIG. 12A is a front perspective view of the surgical device shown in FIG. 8 as the clipping mechanism is being attached to the tissue of a human surgical patient.
Figure 12B:
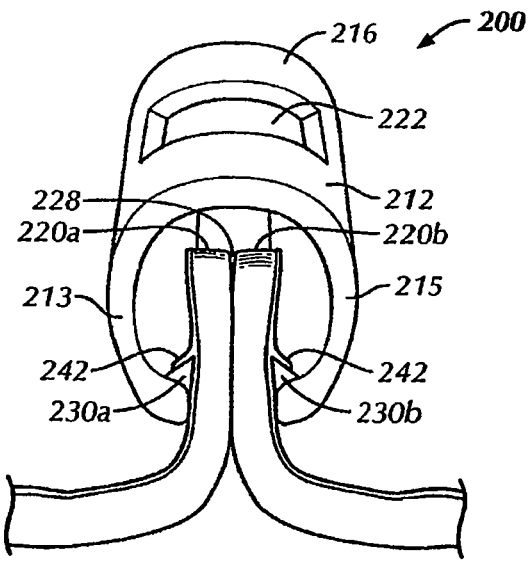
FIG. 12B is a front perspective view of the surgical device shown in FIG. 8 as the clipping mechanism is being attached to the tissue of a human surgical patient.
Figure 12C:
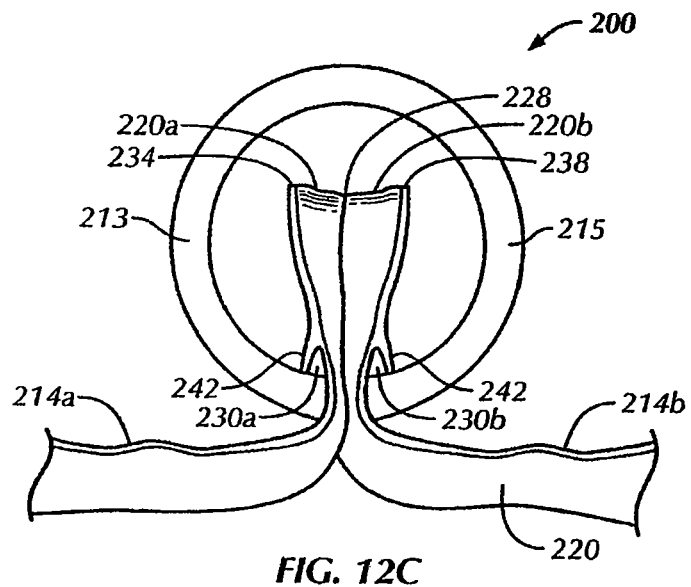
FIG. 12C is a front elevational view of the surgical device shown in FIG. 8 after the clipping mechanism has been attached to the tissue of a human surgical patient.

The clip 212 is also expandable and retractable, such that it can move from a first, flexed open position (as shown in FIGS. 12A-12B) to a second, relaxed closed position (as shown in FIG. 12C). The clip 212 comprises a first clamping member 213 and a second clamping member 215. A distal edge 213a of the first clamping member 213 and a distal edge 215a of the second clamping member 215 are provided for contact with the base sheet 214. As shown in FIG. 10, the distal edges 213a, 215a which form the bottom 218 of the clip are blunt, such that they are configured to compress a patient's tissue 220 without piercing thereof. Since the clip 212 is formed of an elastic and flexible material, the first and second clamping members 213, 215 can be moved away from each other (i.e., to place the clip 212 in the flexed open position as shown in FIG. 12A) or can move toward each other (i.e., to place the clip 212 in the relaxed closed position as shown in FIG. 12C). In the open position, with the first and second clamping members 213, 215 moved away from each other, the clip 212 spans a gap of approximately two tissue thicknesses from distal edge 213a to distal edge 215a. It should be appreciated by those skilled in the art that the size of the gap may be larger or smaller depending upon the size of the clip 212 as well as other factors, such as the size of the wound or incision 228 to be closed.

As shown in FIGS. 10 and 12A-12B, at the bottom 218 of the clip 212, the clip 212 includes a first inwardly extending projection 230a and a second inwardly extending projection 230b. The first and second projections 230a, 230b are each provided on opposing lateral sides of the clip 212. More particularly, the first projection 230a extends inwardly from the distal edge 213a of the first clamping member 213 toward an internal cavity 232 of the clip 212. The second projection 230b extends inwardly from the distal edge 215a of the second clamping member 215, at a location corresponding to the first projection 230a, toward the internal cavity 232 of the clip 212. The first and second projections 230a, 230b may be formed at the first end 212a, the second end 212b, or at any location between the first and second ends 212a, 212b of the clip 212. For example, the first and second projections 230a, 230b may be formed at or near a central point between the first and second ends 212a, 212b of the clip 212. Alternatively, the first and second projections 230a, 230b may be formed at a location proximate to the first and/or second ends 212a, 212b, respectively. Preferably, each of the first and second projections 230a, 230b has a tapered shape, such that the projection 230a, 230b tapers to a point toward the internal cavity 232 of the clip 212. In an assembled position, as shown in FIG. 12C, the first and second projections 230a, 230b engage the base sheet 214 for clamping of the tissue 220, as described more fully herein.

The base sheet 214 of the closure device 200 is substantially planar in an unused form and has a first end 219 and a second end 221. Referring to FIG. 12A, the base sheet 214 has a first longitudinally extending edge 234 and a second longitudinally extending edge 238, and the first and second longitudinally extending edges 234, 238 define an aperture or channel 239 formed within the base sheet 214. Accordingly, the aperture 239 extends through the base sheet 214 longitudinally from proximate to the first end 219 toward the second end 221 (see FIGS. 8-9).

More specifically, the base sheet 214 is formed from a first flexible elongated base member 214a and a second flexible elongated base member 214b. Preferably, the first and second base members 214a, 214b are connected to each other, such that the base sheet 214 is of a single piece construction. However, it will be understood by those skilled in the art that the first and second members 214a, 214b of the base sheet 214 may be separate from each other. The base sheet 214 and, more particularly, the first and second base members 214a, 214b are flexible so that the closure device 200 may conform to the contours of a patient's cutaneous tissue, subcutaneous tissue or internal organs once attached thereto. Accordingly, in an attached or use position, the shape of the base sheet 214 conforms with the contours of the patient's tissue. If the contours of the patient's tissue are planar, then the base sheet 214 will have a planar shape in the use or attached position. If the contours of the patient's tissue are curved, such as with an internal organ, then the base sheet 214 will appear to have a curved shape in the use or attached position. It will be understood by those skilled in the art that while the first and second base members 214a, 214b shown in FIGS. 8-9 and 12A-12C have a generally linear and rectangular shape, the first and second base members 214a, 214b may be of any shape or size necessary to meet the situational demands of the particular surgical procedure to be performed and the particular wound or incision to be closed.

A bottom surface 217 of the base sheet 214 is provided for contact with the patient's tissue 220 proximate to the respective sides of the incision 228. Prior to commencement of a surgical procedure, the base sheet 214 is attached to the area to be closed. Specifically, the first base member 214a is oriented on the patient's tissue 220 on one side of the wound or incision 228 to be made and closed, while the second base member 214b is oriented on the opposing side of the wound or incision 228 to be made and closed. When the first and second base members 214a, 214b are properly situated on a patient's tissue 220, the first longitudinally extending edge 234 of first base member 214a will align with and be situated adjacent to one side of the incision 228, while the second longitudinally extending edge 238 of second base member 214b will align with and be situated adjacent to the opposing side of the incision 228 with the first and second longitudinally extending edges 234, 238 facing each other. More particularly, when the base sheet 214 is properly situated on a patient's tissue 220, the aperture 239 aligns with the incision 228.

The first and second base members 214a, 214b each include at least one pocket 242 (FIGS. 9 and 12A) and, more preferably, include a plurality of spaced-apart pockets 242. Specifically, a plurality of pockets 42 are formed on the first base member 214a proximate to the first longitudinally extending edge 234 and a plurality of pockets 42 are formed on the second base member 214b proximate to the second longitudinally extending edge 238. The pockets 242 are formed on the first and second base members 214a, 214b at spaced-apart locations along a length of the first and second base members 214a, 214b. Preferably, the location of each pocket 242 formed on the first base member 214a corresponds to or is aligned with the location of each pocket 242 formed on the second base member 214b. Thus, each pocket 242 formed on first base member 214a has a corresponding pocket 242 formed on second base member 214b.

The pockets 242 may have any appropriate shape, such as rectangular, ovular, circular, and the like. Preferably, the pockets 242 are generally rectangular in shape. The pockets 242 are made of the same material as remainder of the base sheet 214. However, it will be understood by those skilled in the art that the pockets 242 may be made of another appropriate material.

Each pocket 242 is completely secured to the first and second base members 214a, 214b, except for one open side or area of the pocket 242. Thus, each pocket has an open end 242a and a closed end 242b. The side or area of each pocket 242 that is not secured to the first and second base members 214a, 214b defines a recess or opening 244 that extends from the open end 242a toward the closed end 242b of the pocket 242. The opening 244 is of a sufficient size and of a proper shape to receive and contain the first projection 230a or the second projection 230b of the clip 212.

The clipping mechanism 211 and the base sheet 214 are preferably both bio-absorbable and made of materials that are absorbable by human or animal tissue. For example, each clip 212 may be made of poly glycolic acid (PGA), poly lactic acid (PLA), poly lactic co-glycolic acid (PLGA), hydrolytically-degradable polyester urethane, poly-(glycolide-caprolactone) (PCL), or any combination thereof. It should be understood by those skilled in the art that the clip 212 may be made of any appropriate bio-absorbable material. The base sheet 214 may be made of, for example, degradable polyesters, degradable polyurethanes, hyaluronic acid, carboxymethylcellulose, hydrolytically-degradable polyester urethane, oxidized regenerated cellulose, nucleic acids, collagen, chitosan, fibrin, or any combinations thereof. It should be understood by those skilled in the art that the base sheet 214 may be made of any appropriate degradable film material.

The closure device 200 may be used to close incisions in cutaneous tissue, subcutaneous tissue, including soft tissue, and internal organs. The closure device 200 may be used for a surgical procedure performed on a human patient and for a veterinary surgical procedure. Preferably, the closure device 200 is generally utilized to close an incision 228 made in subcutaneous tissue 220 during a surgical procedure, such as a C-section. Referring to FIGS. 8-9 and 12A-12C, the closure device 200 is shown attached to the subcutaneous tissue 220 of a human surgical patient, which has been incised and the incision 228 is to be closed. While the subcutaneous tissue 220 of a human patient is used for illustrative purposes in the present embodiment, it will be apparent to one of ordinary skill in the art that the closure device 200 may be employed on various types of tissue, such as cutaneous tissue, and on any internal organ, such as a kidney, lung, liver, heart, etc., and on various types of mammalian and animal patients.

To attach the closure device 200 to the tissue 220, the base sheet 214 is first applied or attached to the tissue 220, such that the aperture 239 corresponds to the intended line of incision. Thus, preferably, the first and second base members 214a, 214b are applied to the tissue 220 prior to the incising of the tissue 220.

As described above, the first and second base members 214a, 14b are placed on the patient's tissue 220 at corresponding locations on either side of the wound or incision 228 to be made and closed, such that the longitudinally extending longitudinally extending edge 234 of first base member 214a will align with and be adjacent to one side of the incision 228, while the longitudinally extending edge 238 of second base member 214b will align with and be adjacent to the other side of the incision 228. The pockets 242 formed on the first base member 214a should be aligned with the pockets 242 formed on the second base member 214b. The first and second base members 214a, 214b should extend at least along the entire length of the desired incision 228. A plurality of first and second base members 214a, 214b may be used to ensure that the base sheet 214 extends the entire length of the desired incision 228.

While it is preferred that the base sheet 214 be attached to the tissue 220 prior to incising thereof, it will be understood by those skilled in the art that the first and second base members 214a, 214b could be applied to the tissue 220 after the incision 228 is made, such that the first base member 214a is situated on one side of the incision 228, while the second base member 214b is situated on the other side thereof, such that the incision 228 is oriented within the aperture 239.

After the base sheet 214 has been applied to the tissue 220, the tissue 220 which is aligned with the longitudinally extending edges 234, 238 of the aperture 239 may then be incised and the surgical procedure completed. Next, a clip 212 is to be placed on and attached to the base sheet 214, and specifically to the first and second base members 214a, 214b, as shown in FIGS. 9 and 12A-12C, to commence closure of the incision 228. Before placement of the clip 212 on the first and second base members 214*a*, 214*b*, the first and second clamping members 213, 215 are manually spread apart from each other. The surgeon may maintain the first and second clamping members 213, 215 in the spread-apart position, as shown in FIG. 12A, simply by using his or her hands, or may do so with the assistance of a surgical instrument, such as surgical tweezers 246. Specifically, the surgeon may insert surgical tweezers 246 through the opening 222 into the internal cavity 232 of the clip 212 to maintain the first and second clamping members 213, 215 of the clip 212 in a spread-apart position, such that the clip 212 is in the flexed, open position, as shown in FIG. 9.

The first and second clamping members 213, 215 are then manually oriented on either side of the incision 228, and then the clip 212 is brought into contact with the base sheet 214. Specifically, the first clamping member 213 is first oriented on and brought into direct contact with the first base member 214*a*, and then the second clamping member 215) is oriented on and brought into direct contact with the second base member 214*b* (FIGS. 12A-12B). Alternatively, the first and second clamping members 213, 215 may be brought into contact with first and second base members 214*a*, 214*b*, respectively, simultaneously. In this position, the first and second clamping members 213, 215 extend in a direction parallel to the incision 228 and the longitudinally extending edges 234, 238 of the first and second base members 214*a*, 214*b*.

When the clip 212 is properly situated on the first and second base members 214*a*, 214*b*, the first projection 230*a* extending from the distal edge 213*a* of the first clamping member 213 engages one of the pockets 242 formed on the first base member 214*a*, and the second projection 230*b* extending from the distal edge 215*a* of the second clamping member 215 engages a corresponding pocket 242 formed on the second base member 214*b* (see FIG. 12B). Also, the opening 222 of the clip 212 is oriented above and spaced-apart from the incision 228. The surgeon then releases the clip 212, such that the clip 212 automatically moves to the closed position to pinch or clamp the tissue 220, as shown in FIG. 12C, thereby closing at least a portion of the incision 228. It should be understood by those skilled in the art that more or less of the tissue 220 could be captured within the internal cavity 232 of the clip 212 than shown in FIG. 12C. For example, the tissue 220 could fill the entire internal cavity 232 of the clip 212.

Also, in a further embodiment, the clip 212 may be attached to the base sheet 214 directly by a compression fit, without utilizing the pockets 242 or the first and second projections 230*a* and 230*b*. Specifically, according to this embodiment, the compressive force of the clip 212 is sufficient to secure the clip 212 to the base sheet 214.

Specifically, because of the elasticity of the clip 212, when the clip 212 is placed on the base sheet 214 and the first and second clamping members 213, 215 are released, the first and second clamping members 213, 215 automatically come together, moving the clip 212 into the closed position. This action causes the distal edges 213*a*, 215*a* of the first and second clamping members 213, 215, respectively, to apply pressure to the patient's tissue 220 around the incision 228, as shown in FIG. 12C, and the first and second edges 220*a*, 220*b* of the incised tissue 220 are brought toward each other. This clamping action applies positive pressure to the tissue 220, which reduces the blood content of the tissue and minimizes blood loss upon cutting of the tissue. Specifically, the clip 212 maintains positive pressure on the tissue 220 until hemostasis is achieved. Preferably, hemostasis is achieved immediately after the closure device 10 is in place. Further, the clip 212 everts the tissue, as shown in FIGS. 12A-12C, thereby holding the incised tissue in an upward direction to reduce the risk of any hidden bleeding at the incision site.

Also, as the surgeon is positioning the clip 212 on the base sheet 214, he may use any type of surgical instrument to lift and pull the tissue 220 into the internal cavity 232 of the clip 212 in order to ensure complete closure of the incision 228. For example, referring to FIG. 9, surgical tweezers 250 may be inserted through the first and/or second end 212*a*, 212*b* of the clip 212 to pull the tissue 220 on either side of the incision 228 into the internal cavity 232 of the clip 212. In one embodiment, at least a portion of the internal cavity 232 of the clip 212 is coated with an adhesive, such that the tissue 220 will be better secured in the clip 212.

This procedure may then be repeated with as many clips 212 as necessary to close the incision 228 by attaching a plurality of clips 212 to the first and second base members 214*a*, 214*b* along the entire length of the incision 228 in an overlapping manner (see FIG. 8). For example, a first clip 212 may be applied to the tissue 220 and the first and second base members 214*a*, 214*b* as described above. Then, a second clip 212 may be applied to the tissue 220 and the first and second base members 214*a*, 214*b* in the same manner. The second clip 212 should be positioned immediately after the first clip 212, such that the finger 226 of the first clip 212 engages and is received within the indentation 224 of the second clip 212, and the first and second projections 230*a*, 230*b* of the second clip 212 engage with a different pair of corresponding pockets 242 formed on the first and second base members 214*a*, 214*b*, respectively.

Figure 13:
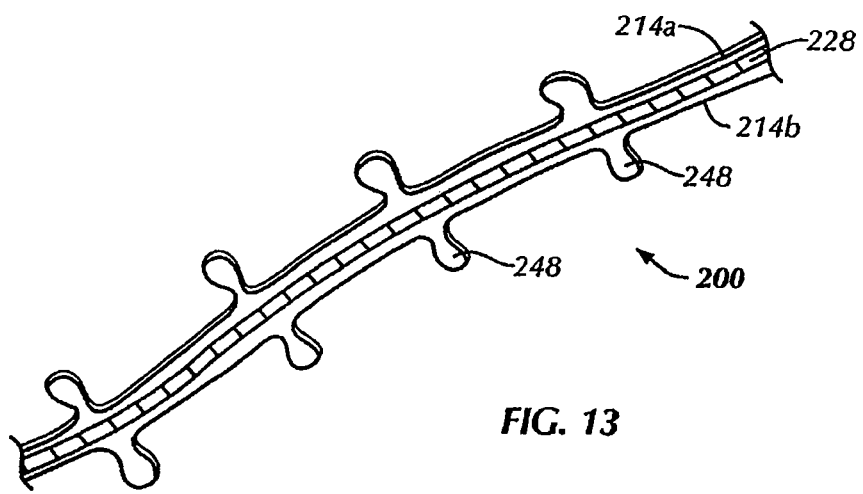
FIG. 13 is top perspective view of a patch in accordance with a fourth preferred embodiment of the present invention.

In another embodiment, shown in FIG. 13, the first and second base members 214*a*, 214*b* may include a plurality of corresponding loops 248 which project outwardly away from the incision 228. The loops 248 may be made of the same bio-absorbable material that forms the remainder of the base sheet 214 or, alternatively, the loops 248 may be made of a different bio-absorbable material. To close the incision 228, the first and second projections 230*a*, 230*b* of the clip 212 may engage loops 248 formed on first and second base members 214*a*, 214*b*, such that the first and second edges 220*a*, 22*b* of the incised tissue 220 are pulled toward each other.

Figure 14:
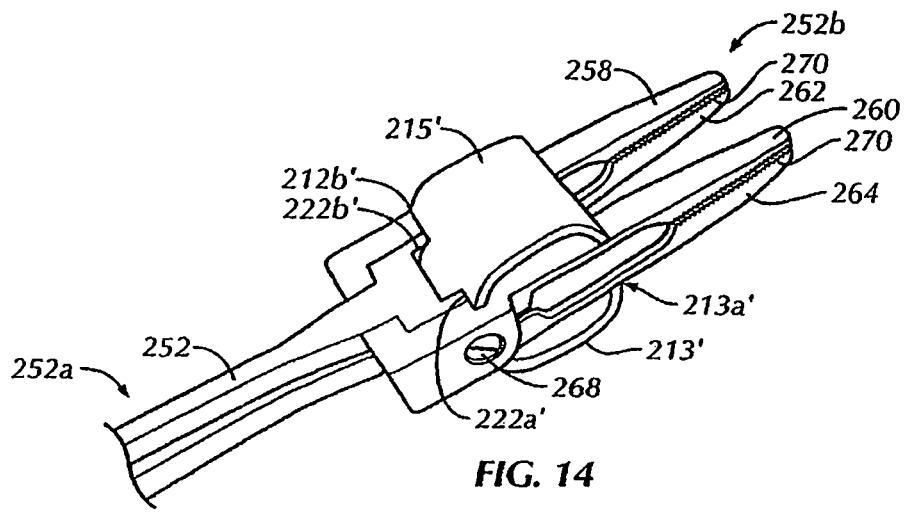
FIG. 14 is a top perspective view of a clipping mechanism and applicator of a fifth preferred embodiment of the present invention, in a closed position.
Figure 15:
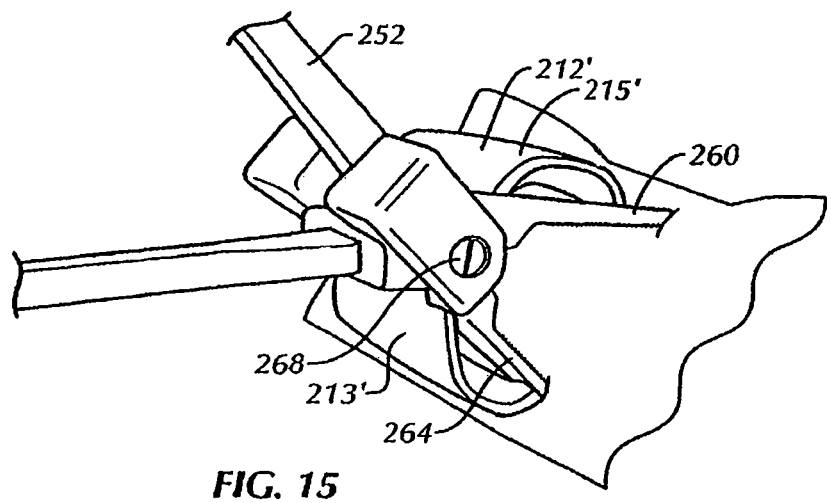
FIG. 15 is a side perspective view of the clipping mechanism and applicator shown in FIG. 14, in a partially open position.
Figure 16:
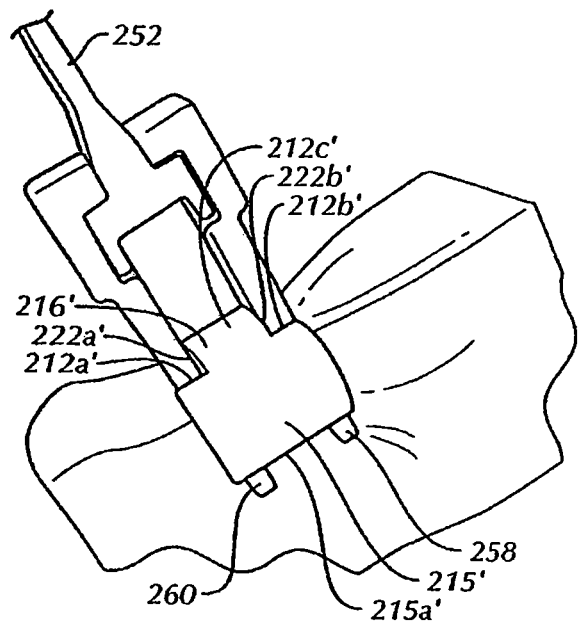
FIG. 16 is front perspective view of the clipping mechanism and applicator shown in FIG. 14, in a partially open position.

In a further embodiment, the closure device 200 and, particularly the clipping mechanism 211, includes a clip 212', as shown in FIGS. 14-16, in place of the clip 212. The clip 212' includes a first clamping member 213' and a second clamping member 215', and respective distal clamping edges 213*a*' and 215*a*' provided for contact with the first and second base members 214*a*, 214*b* to clamp the patient's tissue 220. A first opening 222*a*' and a second opening 222*b*' are formed in a top 216' of the clip 212'. The clip 212' is preferably bio-absorbable. More particularly, the first opening 222*a*' is formed in the top 216' proximate to a first end 212*a*' of the clip 212' and the first opening 222*a*' extends toward a center 212*c*' of the clip 212'. The second opening 222*b*' is formed in the top 216' proximate to a second end 212*b*' of the clip 212' and also extends toward the center 212*c*' of the clip 212'. The first and second openings 222*a*' and 222*b*' remain spaced apart from each other.

Figure 17:
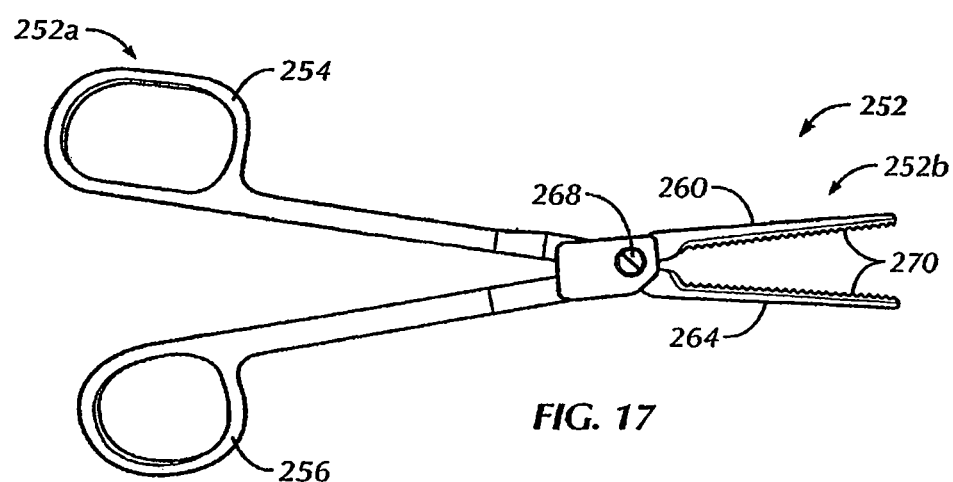
FIG. 17 is side elevational view of the applicator shown in FIG. 14, in an open position.
Figure 18:
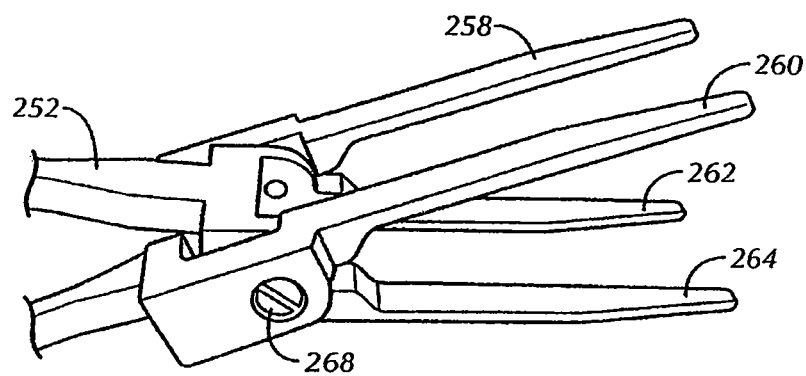
FIG. 18 is an enlarged side elevational view of a portion of the applicator shown in FIG. 17.
Figure 19:
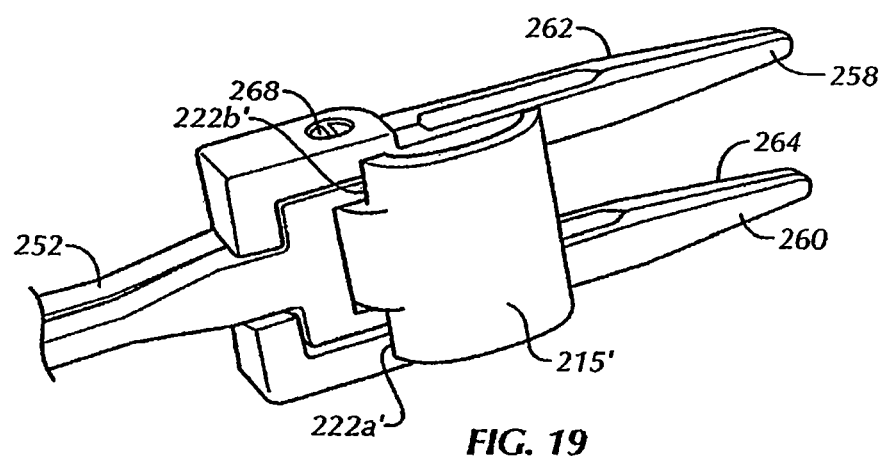
FIG. 19 is an enlarged bottom perspective view of a portion of the applicator shown in FIG. 17 and the clipping mechanism shown in FIG. 14, in a closed position.

A surgical applicator 252 may be used to spread the first and second clamping members 213', 215' apart from each other and to apply the clip 212' to a base sheet 214 and the patient's tissue 220, as shown in FIGS. 14-16. Referring to FIGS. 17-19, the applicator 252 includes a first end 252*a* and a second end 252*b*. The first end 252*a* is provided with a first handle 254 and a second handle 256 through which the fingers of the surgeon are inserted for holding and manipulating the applicator 252. At the second end 252*b* are provided a first application member 258, a second application member 260, a third application member 262 and a fourth application member 264. The first application member 258 is positioned directly opposite and configured to contact the third application member 262. The second application member 260 is positioned directly opposite and configured to contact the fourth application member 264.

The application members 258, 260, 262, 264 are all secured to each other at a pivot point 268, to which the handles 254, 256 are also secured. Thus, the application members 258, 260, 262, 264 are all pivotal relative to each other, and movement of the application members 258, 260, 262, 264 can be achieved by movement of the handles 254, 256. At least a portion of an interior surface of each of the application members 258, 260, 262, 264 is provided with teeth 270 for enhanced gripping by the applicator 252.

In a closed position of the applicator 252, as shown in FIG. 14, the handles 254, 256 are proximate to each other, the first and third application members 258, 262 are proximate to and in contact with each other, and the second and fourth application members 260, 264 are proximate to and in contact with each other. In an open position of the applicator 252, as shown in FIGS. 15-18, the handles 254, 256 are spaced away from each other, the first and third application members 258, 262 are spaced away from each other, and the second and fourth application members 260, 264 are spaced away from each other.

To apply the clip 212', the applicator 252 engages the clip 212' in the closed position, as shown in FIG. 14. Specifically, the first and third application members 258, 262 engage the second opening 222b' and the second and fourth application members 260, 264 engage the first opening 222a'. The surgeon may then move the applicator 252 into the open position by moving the handles 254, 256 to spread the handles 254, 256 apart from each other. Such movement causes the first and third application members 258, 262 and the second and fourth application members 260, 264 to pivot and spread apart from each other. In turn, the first and second clamping members 213', 215' of the clip 212' are spread apart or moved away from each other.

Specifically, in the open position of the applicator 252, the third and fourth application members 262, 264 engage the distal edge 213a' of the first clamping member 213', and the first and second application members 258, 260 engage the distal edge 215a' of the second clamping member 215', causing the distal edges 213a' and 215a' to move away from each other. The clip 212' is thus placed into a flexed, open position, as shown in FIG. 15, for positioning on and attachment to the base sheet 214. Once the clip 212' is secured to the base sheet 214, the applicator 252 may be moved back to the closed position, causing the first and second clamping members 213' and 215' to move toward each other and placing the clip 212' in a relaxed, closed position for clamping the tissue 220.

The clips 212, 212' begin to lose their clamping force over the course of two days. As each clip 212, 212' dissolves or degrades, the shape of the clip 212, 212' does not change. More particularly, as the clipping mechanism 211 degrades, the thinner portions of the clips 212, 212' begin to degrade first. The clipping mechanism 211 also lacks any exposed sharp edges, such that there is no risk of harm by such edges to the patient's tissue or to the surgeon using the device 200. The closure device 200 is also relatively simple to use and the clipping mechanism 211 can be applied by a surgeon without any assistance.

Various ways for attaching the base sheet 12, 112, 214 to the patient's tissue 31, 220 are envisioned, such as wet or dry adhesives; barbs; suction cups or patterns; heat, ultrasound or other energy-based methods; static means; and the like. Such attachment means are provided on the surface of the base sheet 12, 112, 214 in contact with the patient's tissue 31, 220. The attachment method/ways that are utilized will generally depend upon the particular surgery being performed. Preferably, an adhesive is used. More particularly, regarding the base sheet 12, an adhesive layer 13 may be coated upon or otherwise adhered to the surface 12a of the base 12. Regarding the base sheet 214, an adhesive layer 266 may be coated upon or otherwise adhered to the surface 217 of the first and second base members 214a, 214b. Preferably, the adhesive is a meta-adhesive or a protein-based adhesive that functions in wet or high turbulence environments. Such an adhesive is particularly structured for soft tissue deployment, thereby facilitating the making or closure of a surgical incision on soft tissue. For example, the adhesive used may be made of collagen, cyanoacrylate, functional carboxylic acid groups, polyvinylpyrrolidone, or one of a number of hydrogels. Preferably, the adhesive is made of functional carboxylic acid groups. If barbs are used, the surfaces 12a, 217 in contact with the tissue 31, 220 may be provided with a plurality of bio-absorbable barbs (not shown) extending generally outwardly away from the surfaces 12a, 217. Upon contact with the tissue 31, 220, the barbs are bio-absorbed by the patient's tissue 31, 220, such that the base 12, 112, 214 remains secured thereto.

The base sheet 12, 112, 214 serves to block scarring that may occur between portions of adjacent tissue. In the context of cesarean sections, the base sheet 12, 112, 214 blocks adhesions between the uterus and the bladder.

Figure 20:
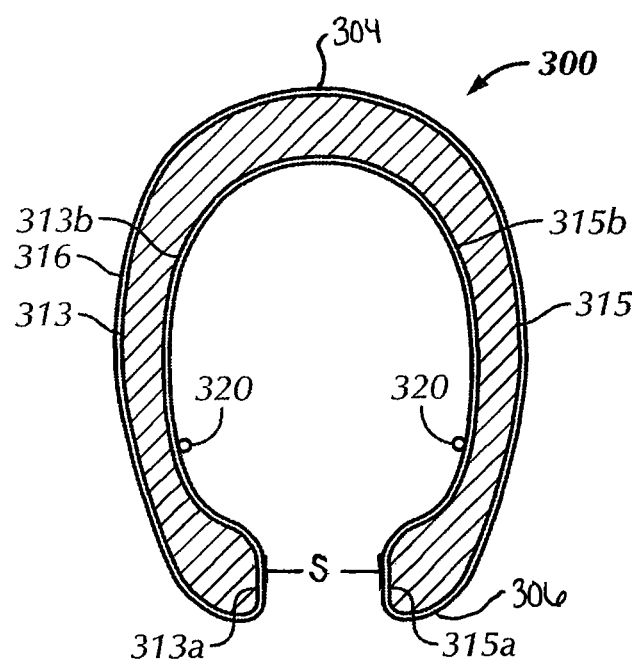
FIG. 20 is a cross-sectional view of a clipping mechanism of a sixth preferred embodiment of the present invention, in an open position.

In another embodiment, shown in FIG. 20, the present invention is directed to a bio-absorbable and hemostatic clip 300 which does not require an associated base sheet for closure of a surgical wound. Rather, the material that would generally form the base sheet 12, 112, 214 is incorporated into the clip 300, such that the clip 300 may reduce tissue adhesion and function independently of a base sheet to directly grip tissue. Preferably, at least a portion of the body of the clip 300 is formed of materials that are absorbable by human or animal tissue. For example, the clip 300 may be made of poly glycolic acid (PGA), poly lactic acid (PLA), poly lactic co-glycolic acid (PLGA), hydrolytically-degradable polyester urethane, poly-(glycolide-caprolactone) (PCL), chitosan, or any combination thereof. It will be understood by those skilled in the art that the clip 300 may be made of any appropriate bio-absorbable material or biologic material At least a portion of the body of the clip 300 also preferably includes a coating layer 316 formed of the bio-absorbable material of base sheets 12, 112, 214. Preferably the coating layer 316 is formed around an outer circumference of the clip 300. Preferably, the coating layer 316 is formed of a degradable polyester block copolymer with urethane linkages, fibrin or fibrin products, cellulose or cellulose products, or hyaluronic acid. More preferably, the coating layer 316 is formed of a degradable polyester block copolymer with urethane linkages. It will be understood by those skilled in the art that the clip 300 need not include the coating layer 316 and, alternatively, a base sheet 12, 112, 214 may be placed over the clip 300 or a series of clips 300 after they have been attached to tissue to provide a barrier to tissue adhesions. Alternatively, the clip 300 may be at least partially or wholly formed of a bio-absorbable material, such as that which forms the coating layer 316.

Figure 21:
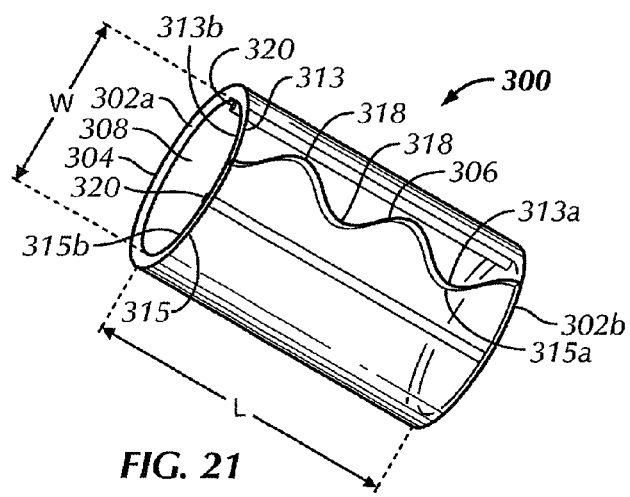
FIG. 21 is an enlarged bottom perspective view of the clipping mechanism shown in FIG. 20, in a closed position.

Referring to FIGS. 20-21, each clip 300 has an elongated shape and comprises a one-piece clip comprising a first end 302a, a second end 302b, a top 304 and a bottom 306. The clip 300 has a first clamping member 313 and a second clamping member 315, each with a respective distal clamping edge 313a, 315a provided for direct contact with the tissue. At a position spaced apart from the respective distal clamping edges 313a, 315a, respective interior surfaces 313b, 315b of the first and second clamping members 313, 315 are provided with a respective elongated rib 320. In the present embodiment, the first and second elongated ribs 320 preferably extend along the entire length L of the clip 300. However, it will be understood by those skilled in the art that the ribs 320 may span only a portion of the overall length L of the clip.

In the present embodiment, the length L of the clip 300 is approximately 7 to 17 mm. Similar to the clip 212, the clip 300 is also expandable and retractable, such that it can move from a first, flexed open position (as shown in FIG. 20), where the first and second clamping members 313, 315 are moved away from each other, to a second, relaxed closed position (as shown in FIG. 21), where the first and second clamping members 313, 315 are moved toward each other. The clip 300 has a generally circular cross sectional shape. In the closed position, as shown in FIG. 21, the clip 300 has a width W of approximately 6 to 12 mm. Referring to FIG. 20, in the open position, in the present embodiment, the span S between the distal clamping edges 313a, 315a is approximately 0.5 to 1 cm. It will be understood by those skilled in the art that the dimensions of the clip 300 may vary depending upon the requirements of the particular application for which the clip 300 is used.

As shown in FIG. 21, the distal clamping edges 313a, 315a of the clip 300 are provided with a plurality of spaced-apart clamping teeth 318. The spaced-apart teeth 318 extend along at least a portion of the length of the respective clamping edge 313a, 315a, but preferably along the entire length of the respective clamping edge 313a, 315a. In the closed position of the clip 300, when the clip 300 is not placed on tissue, the plurality of teeth 318 engage each other in an interlocking fashion, such that the clip 300 has a generally elliptical cross-sectional shape. When the clip 300 is placed on the tissue for closure of an incision, the plurality of teeth 318 engage and clamp the tissue, thereby effectively promoting tissue healing at the site of the incision. The clamping teeth 318 provide the additional advantage of helping to anchor the clip 300 to the tissue. In a preferred embodiment, particularly useful for clamping smooth muscle tissue, the clamping teeth 318 preferably have a sinusoidal form or shape, and are preferably approximately two mm in amplitude, with a period of preferably approximately seven mm. However, it will be understood by those skilled in the art that the form, amplitude, and period of the clamping teeth 318 may vary depending upon the particular type of tissue can be clamped in order to optimize the structure of the clip 300 for specific procedures.

Figure 22:
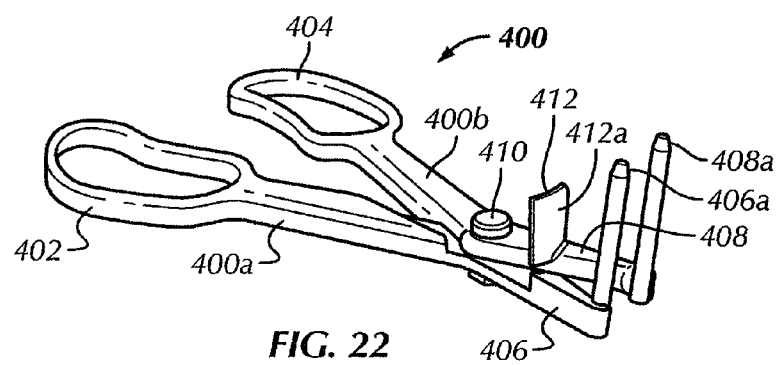
FIG. 22 is a top perspective view of a first type of applicator for the clipping mechanism shown in FIGS. 20-21.
Figure 23:
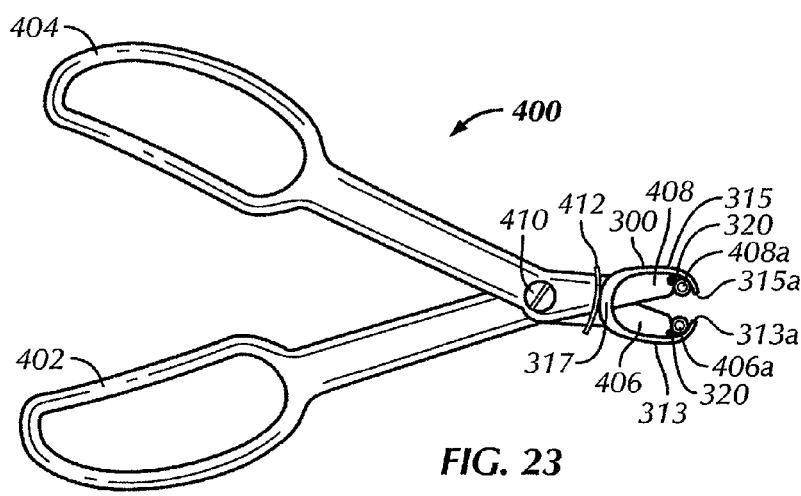
FIG. 23 is a top plan view of the clipping mechanism and applicator shown in FIGS. 20-22, in an engaged position.

Preferably, a surgical applicator is used to apply the clip 300 to the patient's tissue for closure of an incision. One embodiment of the surgical applicator is shown in FIGS. 22-23. Specifically, referring to FIG. 22, the applicator 400 includes a first portion 400a and a second portion 400b. The first portion 400a includes a first handle portion 402 and a first application member 406 extending at an angle from the first handle portion 402. The second portion 400b includes a second handle portion 404 and a second application member 408 extending at an angle from the second handle portion 404. The first and second portions 400a, 400b are rotatably secured to each other at a pivot point 410 situated between the first and second handle portions 402, 404 and the first and second application members 406, 408. Thus, the first and second portions 400a, 400b, along with the first and second application members 406, 408, are pivotal relative to each other by relative movement of the first and second handle portions 402, 404.

The ends of the first and second application members 406, 408 distal from the pivot point 410 include first and second engaging members 406a, 408a, respectively. The first and second engaging members 406a, 408a are in the form of elongated, generally parallel members which extend away from the first and second application members 406, 408, respectively, and are configured to contact the first and second clamping members 313, 315, respectively, of the clip 300. More particularly, the first and second engaging members 406a, 408a are configured to contact and engage the elongated rib 320 of the first and second clamping members 313, 315, respectively, as shown in FIG. 23. At a position in between the pivot point 410 and the second engaging member 408a, the second application member 408 is provided with a securing member 412 having a slightly curved shape for engaging the curved upper portion 317 of the top 304 of the clip 300 during application of the clip 300 to a patient's tissue.

To apply the clip 300 to a patient's tissue, the first and second engaging members 406a, 408a are initially brought into contact with and engage the interior surfaces of the first and second clamping members 313, 315, respectively. In the initial application position, the first and second handle portions 402, 404 are spread apart from each other and the top 304 of the clip 300 rests against a bottom surface 412a of the securing member 412, such that the clip 300 is securely held in place. The first and second handle portions 402, 404 are then brought towards each other, such that the first and second handle portions 402, 404 are proximate to each other and the first and second application members 406, 408 pivot and spread apart from each other. In turn, the first and second engaging members 406a, 408a cause the first and second clamping members 313, 315 of the clip 300 to spread apart or move away from each other, thereby placing the applicator 400 and the clip 300 in open positions.

Specifically, in an open position of the applicator 400 (or in a partly open position as shown in FIGS. 22-23), the first and second engaging members 406a, 408a engage the respective distal edges 313a, 315a and the respective elongated rib 320 of the first and second clamping members 313, 315, such that the applicator 400 is secured in place and thereby causing the distal edges 313a, 315a to move away from each other. The clip 300 is thus placed into a flexed, open position for positioning on and attachment to the patient's tissue. FIG. 23, in particular, shows the clip 300 in a partly open position. Once the clip 300 is secured to the patient's tissue, the applicator 400 may be moved back to the closed position, causing the first and second clamping members 313 and 315 to automatically move toward each other and placing the clip 300 in a relaxed, closed position for clamping and applying positive pressure to the tissue. This procedure may then be repeated with as many clips 300 as necessary to close the incision.

Referring to FIG. 24a, there is shown an applicator 500 which enables quick and effective application of a plurality of the clips 300 to a patient's tissue for closure of an incision. The applicator 500 comprises a frame 502, a gripping portion or a hand grip 504, a trigger 506, and a storage or clip chamber 508 which houses or stores a plurality of clips 300. Preferably, the clips 300 are housed in the clip chamber 508 in a stacked fashion, such that the applicator 500 may be sequentially deployed several times, with minimal time in between the deployments.

Figure 26A:
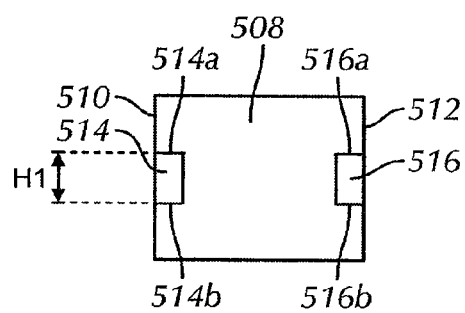
FIG. 26A is a cross-sectional view of the second type of applicator shown in FIG. 24A, taken along line A-A.
Figure 26B:
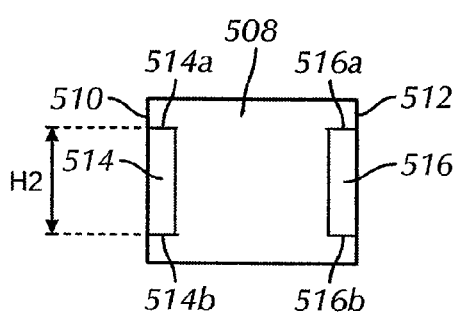
FIG. 26B is a cross-sectional view of the second type of applicator shown in FIG. 24A, taken along line B-B.

Referring to FIGS. 26A-26B, the first and second lateral sides 510, 512 of the clip chamber 508 are provided with a first and second elongated protrusion 514, 516, respectively. The top surface 514a, 516a and bottom surface 514b, 516b of each of the first and second protrusions 514, 516 is an inclined surface, such that each of the first and second elongated protrusions 514, 516 has a varying height. More particularly, at positions distal from an outlet 508*a* of the clip chamber 508, the first and second elongated protrusions 514, 516 have a height H1 which is less than a height H2 of the protrusions 514, 516 at positions proximate to the outlet 508*a* of the clip chamber 508.

Figure 27:
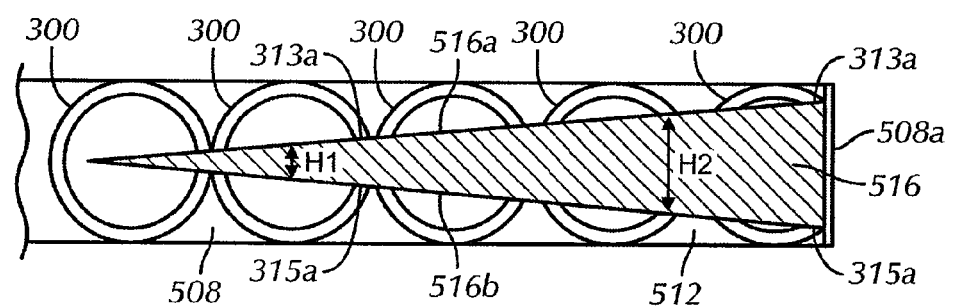
FIG. 27 is a partial cross-sectional view of a portion of the storage chamber of the applicator shown in FIG. 24A, showing the progression of clips through the storage chamber.

The clips 300 are advanced through the clip chamber 508 using an actuator (not shown). As the actuator pushes the rearmost clip 300 forward, each clip 300 advances the adjacent clip 300 in front of it, until the frontmost clip 300 is advanced out of the clip chamber 508 through the outlet 508*a*. As the clips 300 are advanced through the clip chamber 508, each advancing clip 300 engages the first and second protrusions 514, 516. More particularly, the first distal clamping edge 313*a* of each advancing clip 300 engages the respective inclined top surface 514*a*, 516*a* of the first and second protrusions 514, 516, and the second distal clamping edge 315*a* of each advancing clip 300 engages the respective inclined bottom surface 514*b*, 516*b* of the first and second protrusions 514, 516. Each clip 300 is thereby moved from the closed position, to a slightly open position when the clip 300 first engages the first and second protrusion 514, 516. The clips 300 remain in contact with the protrusions 514, 516 as they are advanced through the clip chamber 508 by the actuator. Since the height of the protrusions 514, 516 gradually increases as the protrusions 514, 516 approach the outlet 508*a* of the clip chamber 508, the clips 300 are moved to wider open positions as they approach the outlet 508*a* of the clip chamber 508, as shown in FIG. 27. Accordingly, each clip 300 is in at least a partly open position, preferably the completely open position, upon exiting the clip chamber 508. In the present embodiment, the clip chamber 508 of the applicator 500 preferably stores approximately six to eight clips 300. However, it will be understood by those skilled in the art that the number of clips 300 stored in the chamber 508 may vary dependent upon the particular application for which the clips 300 and applicator 500 are used.

The trigger 506 has a starting position, as shown in FIG. 24*a*, and an activated position, shown in phantom in FIG. 24*a*. When the trigger 506 is squeezed or moved from the starting position to the activated position, the first clip 300 of the stack—that is, the clip 300 most proximate to the outlet 508*a* of the chamber 508—is ejected from the chamber 508 through the outlet 508*a* and onto the patient's tissue. As described above, when the clip 300 is being ejected, the clip 300 is maintained in the at least partly or completely open position by protrusions 514, 516. However, upon ejection from the applicator 500, the first and second clamping members 313 and 315 of the clip 300 naturally move toward each other, such that the clip 300 is moves towards the relaxed, closed position for clamping and applying positive pressure to the tissue. The trigger 508 then automatically springs back to the starting position and the next clip 300 in the stack is pushed or moved into a position for ejection.

In one embodiment, shown in FIG. 24*a*, the clip chamber 508 has an extremely elongated shape, with a length L1 of greater than approximately 12 cm and a diameter D of approximately 10 mm, and more preferably, a length of approximately 14 cm and a diameter D of approximately 9 mm. The applicator 500 is thus particularly suited for use in any type of laparoscopic surgery in which relatively small skin incisions of approximately 10 mm in diameter are made. More particularly, the applicator 500 is well suited for use in laparoscopic hysterectomy procedures, in which small incisions of approximately 7 to 15 mm in diameter are made.

In another embodiment, shown in FIG. 24*b*, an applicator 500' comprises a frame 502', a hand grip 504', a trigger 506', and a clip chamber 508' of a shorter length and a greater width than the chamber 508 of the applicator 500. Thus, the chamber 508' has a shorter length than the chamber 508 of the applicator 500. Preferably, the chamber 508' has a length less than approximately 12 cm and, more preferably, a length L2 of approximately 11 cm. The applicator 500' is thus particularly suited for use in surgeries involving larger skin incisions (greater than approximately 1 cm). One particular example of such a surgery is a cesarean section. Other examples include, but are not limited to, knee replacement, hip replacement, and open hysterectomy procedures.

FIGS. 25*a* through 25*e* depict the progression for closure of an incision 520 in tissue 540 using a plurality of clips 300 and the applicator 500'. It will be understood by those skilled in the art that the same procedure may be followed using the applicator 500. A first clip 300 may be applied to the tissue 540 as described above. Specifically, the applicator 500' is positioned over the incision 520, such that the incision 520 is generally aligned with a central axis of the outlet 508*a'* of the chamber 508'. One or more surgical tools, such as standard or laparoscopic forceps, may be used to bring first and second edges 520*a*, 520*b* of the incision 520 toward each other for easier application of the clip 300. For surgeries involving large incisions, such as caesarian sections, surgical forceps may be needed for effective placement of the first two to three clips 300.

Figure 25A:
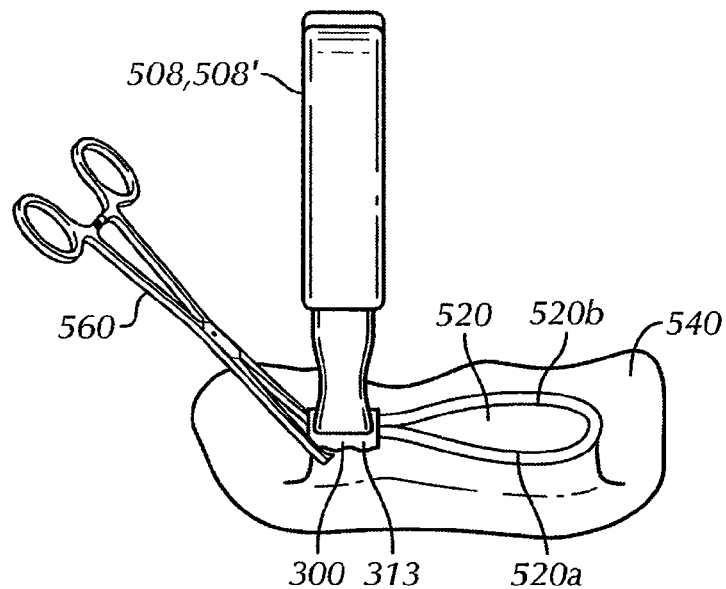
FIG. 25A is a front perspective view of a first clip and application shown in FIGS. 20-23 as the clipping mechanism is being attached to the tissue of a human surgical patient by the applicator.
Figure 25B:
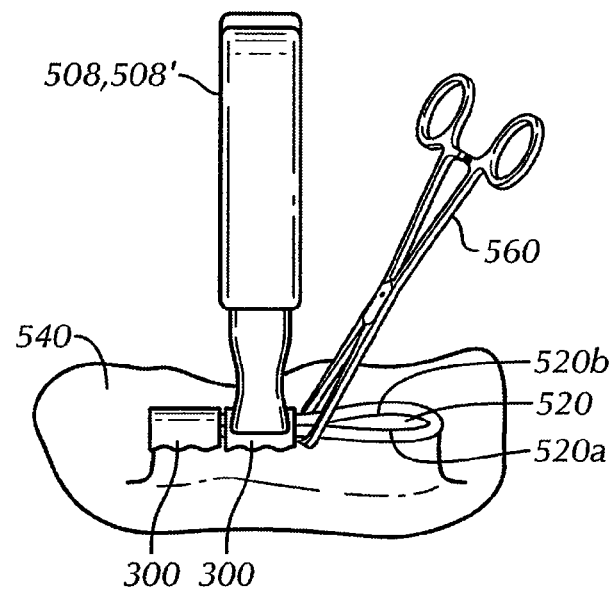
FIG. 25B is a front perspective view of a second clip and application shown in FIGS. 20-23 as the second clipping mechanism is being attached to the tissue of a human surgical patient by the applicator.
Figure 25C:
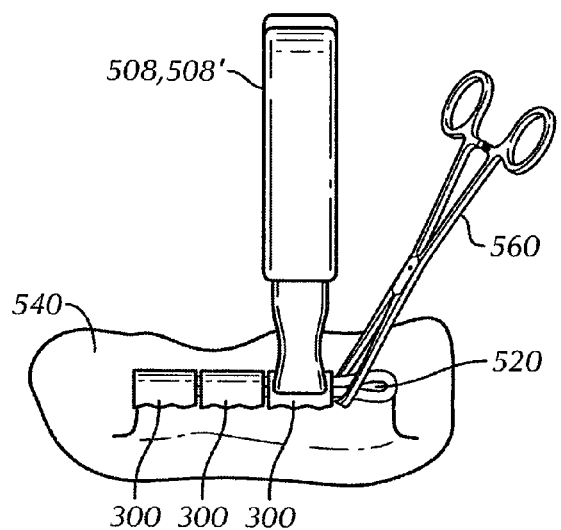
FIG. 25C is a front perspective view of a third clip and application shown in FIGS. 20-23 as the third clip is being attached to the tissue of a human surgical patient by the applicator.
Figure 25D:
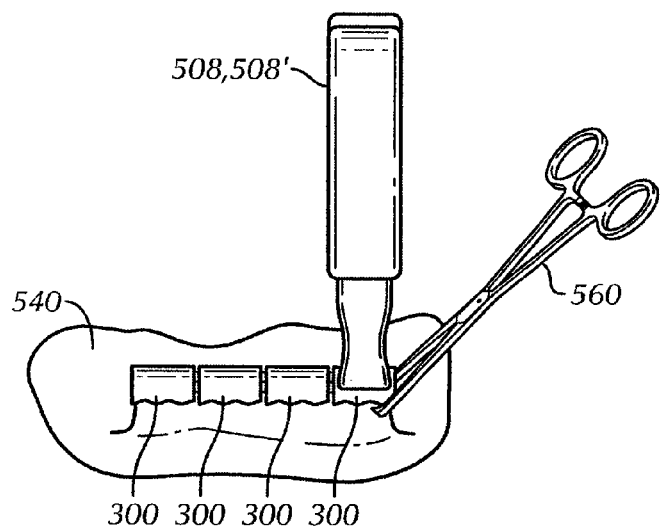
FIG. 25D is a front perspective view of a fourth clip and application shown in FIGS. 20-23 as the fourth clipping mechanism is being attached to the tissue of a human surgical patient by the applicator.
Figure 25E:
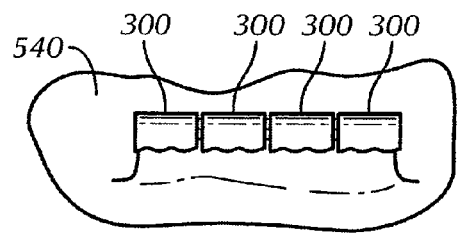
FIG. 25E is a front perspective view of the four clipping mechanisms shown in FIGS. 20-23 having been attached to the tissue of a human surgical patient by the applicator.

The surgeon then squeezes the trigger 506' to place the trigger 506' in the activated position and eject the first clip from the chamber 508'. Upon ejection from the chamber 508', the first distal edge 313*a* of the first clamping member 313 engages the first edge 520*a* of the incised tissue 540 and the second distal edge 315 of the second clamping member 315 engages the second opposing edge 520*b* of the incised tissue 540. The first and second distal edges 313*a*, 315*a* of the clip 300 naturally move toward each other upon ejection from the applicator 500' to place the clip 300 in the closed position. This action causes the distal edges 313*a*, 315*a* of the first and second clamping members 313, 315, respectively, to apply pressure to the patient's tissue 540 around the incision 520, as shown in FIG. 25*a*, and the first and second edges 520*a*, 520*b* of the left end of the incised tissue 540 are brought toward each other. This clamping action applies positive pressure to the tissue 540 and facilitates closure of the incision 520. Referring to FIGS. 25*b*-25*e*, the above-described procedure is repeated and each subsequent clip 300 is placed directly adjacent to the previously applied clip 300, until the entire length of the incision 520 is covered by the plurality of clips 300, as shown in FIG. 25*e*.

The device 10, 100, 200, 300 provides for quick and accurate closure of wounds or incisions made in cutaneous tissue, subcutaneous tissue, including soft tissue, and internal organs, thereby decreasing the risk of infection that is always associated with an open wound. Specifically, the device 10, 100, 200, 300 may reduce surgery times by up to two minutes per inch of incision on the cutaneous tissue (i.e., the skin) and by an even greater amount for incisions on internal tissues. The device 10, 100, 200, 300 is therefore particularly beneficial for use in internal procedures, such as cesarean sections, which traditionally require a relatively long period of time to close incisions made in the uterus. For example, for cesarean sections, it traditionally takes approximately ten minutes to close the uterus using sutures, while the actual step of removing the baby from the mother's uterus only takes approximately one minute. Using the device 10, 100, 200, 300, it would take only two minutes to close the incision made in the uterus. Further, the device 10, 100, 200, 300 does not place the high degree of localized stresses upon the uterine wall as is applied by sutures.

After closure of an incision, there is no need to remove the device 10, 100, 200, 300. The device 10, 100, 200, 300 remains in place during the healing process because it is self-dissolving or bio-absorbable. However, for the device 10, 100, the slider mechanism 28, the pull tab 30 and the clamping mechanism 36, if used, must be removed after closure. Specifically, the device 10, 100, 200, 300 remains adhered to the tissue and remains in place until the healing process is complete, generally approximately seven days. Thus, the device 10, 100, 200, 300 provides a layer of secondary protection for the wound against contamination during the healing process, thereby dramatically reducing the risk of post-operative infections and adhesions. Further, because the device 10, 100, 200, 300 remains in place post-operatively, subsequent or repeated access to the incised site is easily accomplished.

The device 10, 100, 200, 300 is ultimately passively removed or released from the patient's body by a normal breakdown of the device 10, 100, 200, 300. If the device 10, 100, 200, 300 is used to close subcutaneous or internal tissue, it may be removed by bio-absorption by the tissue, aeration or digestion. If the device 10, 100, 200, 300 is used to close an incision on cutaneous tissue, it may also be actively removed or passively released from the tissue through a natural sloughing of the cutaneous tissue.

It will be appreciated by those skilled in the art that changes could be made to the above described preferred embodiments 10, 100, 200, 300 of the surgical device without departing from the broad inventive concepts thereof. It is understood, therefore, that this invention is not limited to the particular embodiments disclosed, but is intended to cover modifications within the spirit and scope of the present invention as defined by the appended claims.

We claim:

1. A clipping mechanism comprising a plurality of flexible hemostatic clips, each clip comprising a first end, a second end, and a major longitudinal axis therebetween, a top and a bottom, wherein the bottom of each clip includes an indentation extending from a distal edge of the first end of the clip toward the second end of the clip and a finger extending generally outwardly from the second end of the clip, and each clip defines a generally C-shape in a cross-section perpendicular to the major longitudinal axis thereof.

2. The clipping mechanism according to claim 1, wherein the plurality of clips are bio-absorbable.

3. The clipping mechanism according to claim 1, wherein the finger of a first clip engages the indentation of a second clip in an assembled configuration of the clipping mechanism.

4. A wound closure device for closing a surgical wound, the device comprising at least one flexible and bio-absorbable hemostatic clip according to claim 1 for applying pressure to a patient's tissue, the clip further comprising a tissue adhesion resistant coating covering at least a portion of an outer circumference of the clip, such that the clip is configured to be directly attached to the patient's tissue and to reduce tissue adhesion.

5. The wound closure device according to claim 4, wherein the clip is made from one or more materials selected from the group consisting of poly glycolic acid, poly lactic acid, poly lactic co-glycolic acid, hydrolytically-degradable polyester urethane, poly(glycolide-caprolactone), and chitosan.

6. The wound closure device according to claim 5, wherein the coating substantially covers all surfaces of the clip.

7. The wound closure device according to claim 4, wherein the coating layer comprises one or more materials selected from the group consisting of degradable polyester block copolymers with urethane linkages, fibrin or fibrin products, cellulose or cellulose products, or hyaluronic acid.

8. The wound closure device according to claim 4, wherein the coating layer is made from a degradable polyester block copolymer with urethane linkages.

9. The wound closure device according to claim 4, wherein the clip further comprises at least a first clamping member having a first distal edge and a second clamping member having a second distal edge, the first and second distal edges being provided with a plurality of spaced-apart clamping teeth.

10. The wound closure device according to claim 9 further comprising an applicator for applying the clip to the patient's tissue, the applicator comprising a frame, a gripping portion, and a storage chamber configured to store a plurality of clips in a stacked manner.

11. The wound closure device according to claim 10, wherein each of the plurality of clips is in at least a partly open position at an outlet of the storage chamber, the first clamping member of the clip being moved away from the second clamping member of the clip in the at least partly open position of the clip.

12. The wound closure device according to claim 4, wherein the coating substantially covers all surfaces of the clip.

13. The wound closure device according to claim 4, wherein the clip is a one-piece clip.

14. The clipping mechanism according to claim 1, wherein distal edges of the bottom of each clip are blunt, the blunt distal edges being configured to compress a patient's tissue without piercing thereof.

* * * * *